US008367824B2

(12) United States Patent  
Nishino et al.

(10) Patent No.: US 8,367,824 B2  
(45) Date of Patent: *Feb. 5, 2013

(54) PROCESS FOR PRODUCING QUINAZOLIN-4-ONE DERIVATIVE

(75) Inventors: Shigeyoshi Nishino, Yamaguchi (JP); Kenji Hirotsu, Yamaguchi (JP); Hidetaka Shima, Yamaguchi (JP); Takashi Harada, Yamaguchi (JP); Hiroyuki Oda, Yamaguchi (JP)

(73) Assignee: Ube Industries Ltd., Ube-shi, Yamaguchi (JP)

( * ) Notice: Subject to any disclaimer, the term of this patent is extended or adjusted under 35 U.S.C. 154(b) by 756 days.

This patent is subject to a terminal disclaimer.

(21) Appl. No.: 10/502,734

(22) PCT Filed: Jan. 28, 2003

(86) PCT No.: PCT/JP03/00805  
§ 371 (c)(1),  
(2), (4) Date: Jul. 28, 2004

(87) PCT Pub. No.: WO03/064399  
PCT Pub. Date: Aug. 7, 2003

(65) Prior Publication Data  
US 2005/0080262 A1 Apr. 14, 2005

(30) Foreign Application Priority Data

| Jan. 28, 2002 | (JP) | 2002-17957 |
| Feb. 19, 2002 | (JP) | 2002-40929 |
| Mar. 25, 2002 | (JP) | 2002-82607 |
| Jun. 10, 2002 | (JP) | 2002-168443 |
| Jun. 19, 2002 | (JP) | 2002-178661 |
| Aug. 27, 2002 | (JP) | 2002-246657 |
| Nov. 11, 2002 | (JP) | 2002-326752 |
| Dec. 2, 2002 | (JP) | 2002-349456 |

(51) Int. Cl.  
C07D 239/72 (2006.01)
(52) U.S. Cl. ..................... 544/287
(58) Field of Classification Search ............ 544/287; 562/458  
See application file for complete search history.

(56) References Cited

U.S. PATENT DOCUMENTS

| 5,710,158 A * | 1/1998 | Myers et al. ............. 514/266.2 |
| 5,739,330 A * | 4/1998 | Bhattacharya et al. ....... 544/249 |
| 5,962,458 A * | 10/1999 | Lohmann et al. ......... 514/266.21 |
| 7,232,903 B2 * | 6/2007 | Nishino et al. ............. 544/287 |
| 8,133,999 B2 * | 3/2012 | Nishino et al. ............. 544/287 |

FOREIGN PATENT DOCUMENTS

| GB | 1199768 | * | 7/1970 |
| WO | WO 95/19970 A1 | | 7/1995 |
| WO | WO 98/43960 A1 | | 10/1998 |
| WO | WO 02/36587 A2 | | 5/2002 |

OTHER PUBLICATIONS

Surya, H. et. al., "One-pot synthesis of pyrrole derivative . . . ," Tetrahedron Letters, 2001, vol. 42, pp. 6595-6597.*  
Kirk et. al., Encyclopedia of Reagents for Organic Synthesis, John Wiley & Son Ltd., 2001, pp. 1-6.*  
Taylor et. al., Triethyl Orthoformate—Encyclopedia of Reagents for Organic Synthesis, John Wiley & Son Ltd., 2001, pp. 1-6.*  
Ogden, J. R. et. al., "Chemical Engineering Handbook", Research & Education Association, Jan. 1999, p. B-114.*  
Dissociation Constants of Organic Acids, http://ifs.massey.ac.nz/outreach/resources/chem/orgbases.php, Jan. 12, 2010.*  
Nierop, K. G.J. et. al., "Clay and ammonium catalyzed reactions . . . ", Journal of Analytical & Applied Pyrolysis, vol. 63 (2002), pp. 197-208.*  
A. Kamal et al., Synthesis of novel non-cross-linking pyrrolobenzodiazepines with remarkable DNA binding affinity and potent antitumour activity, Chem. Commun., 2001, pp. 437-438.  
D. Boschelli et al., Optimization of 4-Phenylamino-3-quinolinecarbonitriles as Potent Inhibitors of Src Kinase Activity, J. Med. Chem., 2001, vol. 44, pp. 3965-3977.

* cited by examiner

Primary Examiner — James O Wilson  
Assistant Examiner — Alexander R Pagano  
(74) Attorney, Agent, or Firm — Nixon Peabody LLP; Jeffrey L. Costellia

(57) ABSTRACT

A process for producing a quinazolin-4-one compound having the formula:

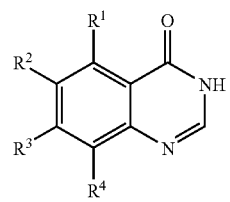

[wherein $R^1$, $R^2$, $R^3$ and $R^4$ each represents a group not participating in the below-mentioned reaction, and $R^1$, $R^2$, $R^3$ and $R^4$ can be combined together to form a ring] which comprises reacting an anthranilic acid derivative having the formula:

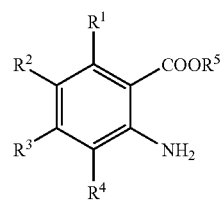

[wherein $R^5$ is a hydrogen atom or a hydrocarbyl group] with a formic acid derivative in the presence of an ammonium carboxylate.

7 Claims, No Drawings

PROCESS FOR PRODUCING QUINAZOLIN-4-ONE DERIVATIVE

FIELD OF THE INVENTION

The present invention relates to a process for preparing a quinazolin-4-one compound from an anthranilic acid compound. The quinazolin-4-one compound is useful as an intermediate or a starting compound for preparing a pharmaceutically active compound or an agricultural chemical.

The invention further relates to a process for preparing a 6-alkoxy-7-aminoalkoxyquinazolin-4-one compound or a 7-alkoxy-6-aminoalkoxyquinazolin-4-one compound from the quinazolin-4-one compound. The 6-alkoxy-7-aminoalkoxyquinazolin-4-one compound and the 7-alkoxy-6-aminoalkoxyquinazolin-4-one compound are useful as intermediates or starting compounds for preparing pharmaceutically active compounds or agricultural chemicals.

The invention furthermore relates to a new quinazolin-4-one compound and then relates to a process for preparing an anthranilic acid compound employable as a starting compound for the production of the quinazolin-4-one compound.

The invention furthermore relates to a process for preparing the above-mentioned anthranilic acid compound from a nitrobenzoic acid compound.

The invention furthermore relates to a process for preparing a 5-alkoxy-4-halogenoalkoxy-2-nitrobenzoic acid compound or a 4-alkoxy-5-halogenoalkoxy-2-nitrobenzoic acid compound from a 3-alkoxy-4-hydroxybenzoic acid compound or a 4-alkoxy-3-hydroxybenzoic acid compound.

BACKGROUND OF THE INVENTION

The following processes are known for preparing a quinazolin-4-one compound from an anthranilic acid compound.

EP 1029853 discloses a process for preparing 6-iodoquinazolin-4-one by reacting 5-iodoanthranilic acid with formamidine acetate in ethanol for 20 hours. This process has problems in that the reaction period is long, and it is necessary to use expensive formamidine in an excessive amount.

Chem. Pharm. Bull., 46, 1926 (1998) describes a process for preparing the quinazolin-4-one by reacting anthranilic acid with formamide. This process has a problem in that teratogenetic formamide is used in an excessive amount.

J. Org. Chem., 18, 138 (1953) describes a process for preparing the quinazolin-4-one by reacting methyl anthranilate and formamide in the presence of an ammonium formate. This process has problems in that teratogenetic formamide is reacted at an elevated temperature in an excessive amount and the yield of the desired compound is low.

Any of the above-described processes have problems, and hence they are not favorable as industrially applicable processes.

WO 01/21594 describes a process for a 6-alkoxy-7-aminoalkoxyquinazolin-4-one compound or a 7-alkoxy-6-aminoalkoxyquinazolin-4-one compound. For instance, ethyl 3-methoxy-4-(3-morpholinopropoxy)-6-aminobenzoate is reacted with formamide to give 6-methoxy-7-(3-morpholinopropoxy)quinazolin-4-one in 68% yield. This process, however, has a problem as an industrially applicable process in that the yield is low, and the teratogenetic formamide is reacted at an elevated temperature in an excessive amount.

JP-A-2001-519788 describes a process for preparing a 5-alkoxy-4-halogenoalkoxyanthranilic acid compound from a 5-alkoxy-4-halogenoalkoxy-2-nitrobenzoic acid compound. For example, methyl 4-(3-chloropropoxy)-5-methoxy-2-nitrobenzoate is reacted with a very excessive amount of iron and ammonium chloride in a mixture of water and methanol, to give methyl 2-amino-4-(3-chloropropoxy)-5-methoxybenzoate (i.e., ethyl 4-(3-chloropropoxy)-5-methoxyanthranilate) in 90% yield.

J. Med. Chem., 44, 3965 (2001) describes a process for preparing a 4-alkoxy-5-halogenoalkoxyanthranilic acid compound from a 4-alkoxy-5-halogenoalkoxy-2-nitrobenzoic acid compound. For example, methyl 5-(3-chloropropoxy)-4-methoxy-2-nitrobenzoate is reacted with a very excessive amount of iron and ammonium chloride in a mixture of water and methanol, to give methyl 2-amino-5-(3-chloropropoxy)-4-methoxybenzoate (i.e., methyl 5-(3-chloropropoxy)-4-methoxyanthranilate) in 93% yield.

These processes, however, have problems as industrially applicable processes in that a very excessive amount of iron is used and a complicated post-treatment process is required.

WO 02/36587 describes a process for preparing a 5-alkoxy-4-halogenoalkoxy-2-nitrobenzoic acid compound from a 3-alkoxy-4-hydroxybenzoic acid compound. For example, ethyl vanillate (i.e., ethyl 4-hydroxy-3-methoxybenzoate) is reacted with 3-bromo-1-chloropropane in an aqueous potassium carbonate solution in the presence of N-butyl-ammonium bromide to produce ethyl 4-(3-chloropropoxy)-3-methoxybenzoate, and the ethyl 4-(3-chloropropoxy)-3-methoxybenzoate is reacted with 70% nitric acid in a mixture of dichloromethane and acetic acid, to give ethyl 4-chloropropoxy-3-methoxy-2-nitrobenzoate in 82% yield (based on the amount of ethyl vanillate).

The aforementioned J. Med. Chem., 44, 3965 (2001) further describes a process for preparing a 4-alkoxy-5-halogenoalkoxy-2-nitrobenzoic acid compound from a 4-alkoxy-3-hydroxybenzoic acid compound. For example, methyl 3-hydroxy-4-methoxybenzoate is reacted with 3-chloropropyl p-toluenesulfonate in an aqueous potassium carbonate solution in the presence of tricaprylmethyl ammonium chloride to produce methyl 3-(3-chloropropoxy)-4-methoxybenzoate, and the methyl 3-(3-chloropropoxy)-4-methoxybenzoate is reacted with 70% nitric acid in a mixture of dichloromethane and acetic acid, to give methyl 5-(3-chloropropoxy)-4-methoxy-2-nitrobenzoate in 61% yield (based on the amount of methyl 3-hydroxy-4-methoxybenzoate).

The above-mentioned process, however, has problems as an industrially applicable process in that the reaction utilizes a complicated two phase reactions, the reaction procedure is complicated, an industrially unfavorable dichloromethane solvent is necessarily employed, the reaction period is long, and the yield is low.

DISCLOSURE OF THE INVENTION

The present invention has an object to provide an industrially advantageous simple process for preparing a quinazolin-4-one compound from an anthranilic acid compound in high yield under moderate conditions.

Further, the invention has an object to provide industrially advantageous simple processes for preparing a 6-alkoxy-7-aminoalkoxyquinazolin-4-one compound and a 7-alkoxy-6-aminoalkoxyquinazolin-4-one in high yields under moderate conditions.

Further, the invention has an object to provide a new quinazolin-4-one compound and an industrially advantageous process for preparing the quinazolin-4-one compound from a new anthranilic acid compound.

Furthermore, the invention has an object to provide an industrially advantageous process for preparing the above-mentioned new anthranilic acid compound from a nitrobenzoic acid compound.

Furthermore, the invention has an object to provide an industrially advantageous process for preparing a 5-alkoxy-4-halogenoalkoxy-2-nitrobenzoic acid compound or a 4-alkoxy-5-halogenoalkoxy-2-nitrobenzoic acid compound from a 3-alkoxy-4-hydroxybenzoic acid compound or a 4-alkoxy-3-hydroxybenzoic acid compound.

The present invention resides in a process for preparing a quinazolin-4-one compound having the formula (2):

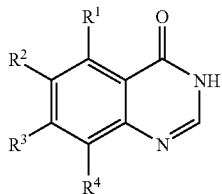

(2)

in which each of $R^1$, $R^2$, $R^3$ and $R^4$ independently represents a group not participating the below-mentioned reaction, or $R^1$, $R^2$, $R^3$ and $R^4$ are combined to form a ring,
which comprises reacting an anthranilic acid compound having the formula (1):

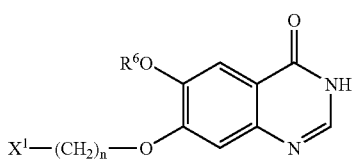

(1)

in which $R^1$, $R^2$, $R^3$ and $R^4$ have the same meaning as above, and $R^5$ represents a hydrogen atom or a hydrocarbyl group,
with a formic acid derivative in the presence of an ammonium carboxylate.

Further, the invention resides in a process for preparing a 6-alkoxy-7-halogenoalkoxyquinazolin-4-one compound having the formula (4):

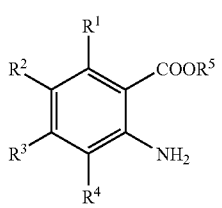

(4)

wherein $R^6$ represents an alkyl group, $X^1$ represents a halogen atom, and n is an integer of 2 to 4,
which comprises reacting a 5-alkoxy-4-halogenoalkoxy-anthranilic acid compound having the formula (3):

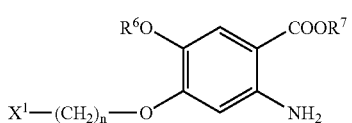

(3)

wherein each of $R^6$, $X^1$, and n has the same meaning as above, and $R^7$ represents a hydrogen atom or a hydrocarbyl group, with a formic acid derivative in the presence of an ammonium carboxylate.

Further, the invention resides in a process for preparing a 7-alkoxy-6-halogenoalkoxyquinazolin-4-one compound having the formula (6):

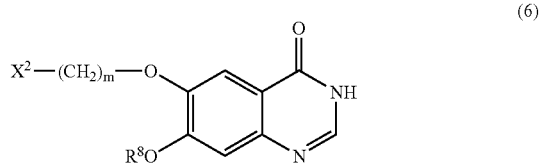

(6)

wherein $R^8$ represents an alkyl group, $X^2$ represents a halogen atom, and m is an integer of 2 to 4,
which comprises reacting a 4-alkoxy-5-halogenoalkoxy-anthranilic acid compound having the formula (5):

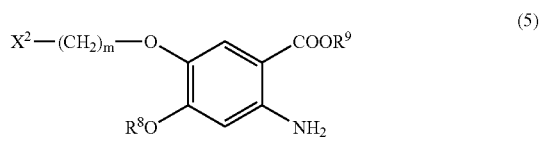

(5)

wherein each of $R^8$, $X^2$, and m has the same meaning as above, and $R^9$ represents a hydrogen atom or a hydrocarbyl group,
with a formic acid derivative in the presence of an ammonium carboxylate.

Further, the invention resides in a new compound embraced in the aforementioned formula (3), namely, 6-methoxy-7-(3-chloroalkoxy)quinazolin-4-one having the formula (7):

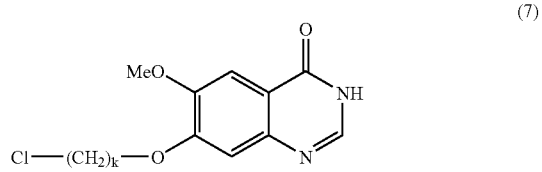

(7)

wherein Me is methyl, and k is an integer of 2 to 4.

Further, the invention resides in a new compound embraced in the aforementioned formula (6), namely, 7-methoxy-6-(3-chloropropoxy)quinazolin-4-one having the formula (8):

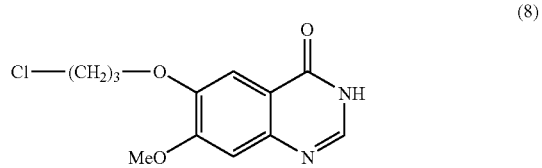

(8)

wherein Me is methyl.

Further, the invention resides in a process for preparing a 5-alkoxy-4-halogenoalkoxyanthranilic acid compound having the formula (3):

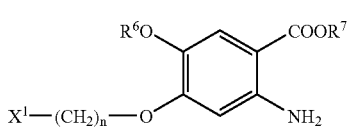
(3)

wherein $R^6$ represents an alkyl group, $R^7$ represents a hydrogen atom or a hydrocarbyl group, $X^1$ represents a halogen atom, and n is an integer of 2 to 4, which comprises reducing a 5-alkoxy-4-halogenoalkoxy-2-nitrobenzoic acid compound having the formula (9):

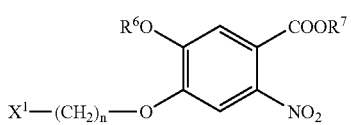
(9)

wherein each of $R^6$, $R^7$, $X^1$, and n has the same meaning as above.

Further, the invention resides in a process for preparing a 4-alkoxy-5-halogenoalkoxyanthranilic acid compound having the formula (5):

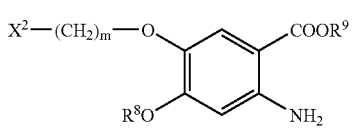
(5)

wherein $R^8$ represents an alkyl group, $R^9$ represents a hydrogen atom or a hydrocarbyl group, $X^2$ represents a halogen atom, and m is an integer of 2 to 4, which comprises reducing a 4-alkoxy-5-halogenoalkoxy-2-nitrobenzoic acid compound having the formula (10):

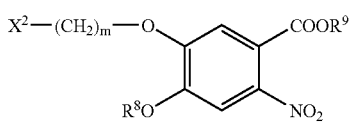
(10)

wherein each of $R^8$, $R^9$, $X^2$, and m has the same meaning as above.

Further, the invention resides in a new compound embraced in the aforementioned formula (3), namely, methyl 5-methoxy-4-(3-bromopropoxy)anthranilate having the formula (11):

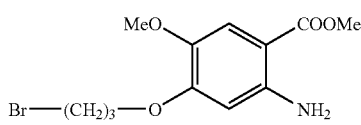
(11)

wherein Me is methyl.

Further, the invention resides in a new compound embraced in the aforementioned formula (3), namely, 5-methoxy-4-chloroalkoxyanthranilic acid having the formula (12):

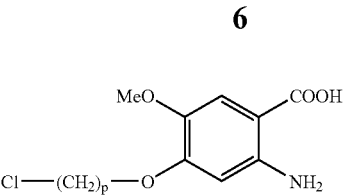
(12)

wherein Me is methyl, and p is 2 or 3.

Further, the invention resides in a new compound embraced in the aforementioned formula (3), namely, methyl 5-methoxy-4-(4-chlorobutoxy)anthranilate having the formula (13):

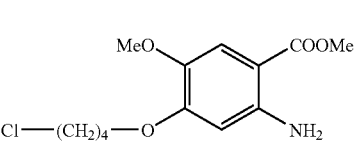
(13)

wherein Me is methyl.

Further, the invention resides in a new compound embraced in the aforementioned formula (5), namely, 4-methoxy-5-(3-chloropropoxy)anthranilic acid having the formula (14):

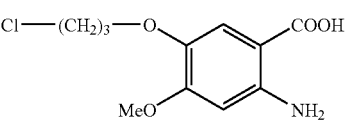
(14)

wherein Me is methyl.

Further, the invention resides in a process for preparing a 5-alkoxy-4-halogenoalkoxy-2-nitrobenzoic acid compound having the formula (9):

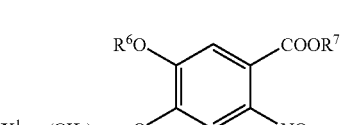
(9)

wherein $R^6$ represents an alkyl group, $R^7$ represents a hydrogen atom or a hydrocarbyl group, $X^1$ represents a halogen atom, and in is an integer of 2 to 4, which comprises:
  a first step of reacting a 3-alkoxy-4-hydroxybenzoic acid compound having the formula (15):

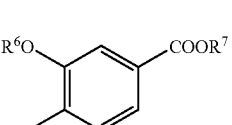
(15)

wherein each of $R^6$ and $R^7$ has the same meaning as above, with a dihalogenoalkane having the formula (16):

(16)

wherein n has the same meaning as above, and each of $X^3$ and $X^4$ represents a halogen atom, in an organic solvent in the presence of a base, to give a 3-alkoxy-4-halogenoalkoxybenzoic acid compound having the formula (17):

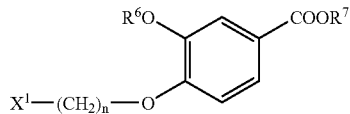

(17)

wherein each of $R^6$, $R^7$, and n has the same meaning as above, and $X^1$ represents a halogen atom corresponding to $X^3$ or $X^4$, and a second step of nitrating the 3-alkoxy-4-halogenoalkoxybenzoic acid compound with nitric acid in the presence of an alkali metal nitrite.

Further, the invention resides in a process for preparing a 4-alkoxy-5-halogenoalkoxy-2-nitrobenzoic acid compound having the formula (10):

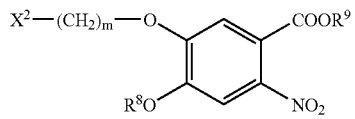

(10)

wherein $R^8$ represents an alkyl group, $R^9$ represents a hydrogen atom or a hydrocarbyl group, $X^2$ represents a halogen atom, and m is an integer of 2 to 4,
which comprises:
a first step of reacting a 4-alkoxy-3-hydroxybenzoic acid compound having the formula (18):

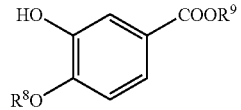

(18)

wherein each of $R^8$ and $R^9$ has the same meaning as above, with a dihalogenoalkane having the formula (19):

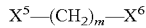   (19)

wherein m has the same meaning as above, and each of $X^5$ and $X^6$ represents a halogen atom,
in an organic solvent in the presence of a base, to give a 4-alkoxy-3-halogenoalkoxybenzoic acid compound having the formula (20):

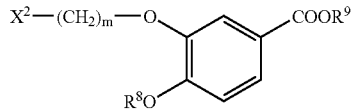

(20)

wherein each of $R^8$, $R^9$, and m has the same meaning as above, and $X^2$ represents a halogen atom corresponding to $X^5$ or $X^6$,
and a second step of nitrating the 4-alkoxy-3-halogenoalkoxybenzoic acid compound with nitric acid in the presence of an alkali metal nitrite.

Further, the invention resides in a new compound embraced in the aforementioned formula (17), namely, methyl 4-(4-chlorobutoxy)-3-methoxybenzoate having the formula (21):

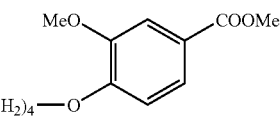

(21)

wherein Me is methyl.

Further, the invention resides in a new compound embraced in the aforementioned formula (9), namely, methyl 4-(4-chlorobutoxy)-5-methoxy-2-nitrobenzoate having the formula (22):

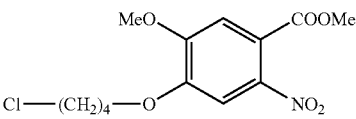

(22)

wherein Me is methyl.

Further, the invention resides in a process for preparing a 6-alkoxy-7-aminoalkoxyquinazolin-4-one compound having the formula (24):

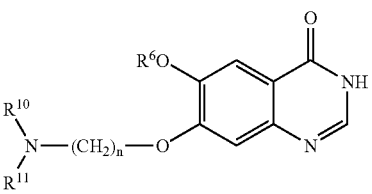

(24)

wherein $R^6$ represents an alkyl group, each of $R^{10}$ and $R^{11}$ represents a hydrogen atom or a hydrocarbyl group which together to form a hydrocarbon ring or a heterocyclic ring, and n is an integer of 2 to 4,
which comprises reacting 6-alkoxy-7-halogenoalkoxyquinazolin-4-one having the formula (4):

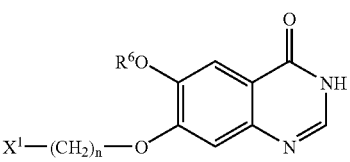

(4)

wherein $R^6$ and n have the same meaning as above, and $X^1$ represents a halogen atom,
with an amine compound having the formula (23)

   (23)

wherein $R^{10}$ and $R^{11}$ have the dame meaning as above.

Furthermore, the invention resides in a process for preparing a 7-alkoxy-6-aminoalkoxyquinazolin-4-one compound having the formula (25):

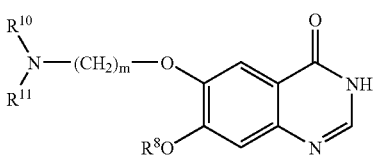

(25)

wherein $R^8$ represents an alkyl group, each of $R^{10}$ and $R^{11}$ represents a hydrogen atom or a hydrocarbyl group which can contain a hetero atom, or $R^{10}$ and $R^{11}$ are combined together to form a hydrocarbon ring or a heterocyclic ring, and m is an integer of 2 to 4, which comprises reacting 7-alkoxy-6-halogenoalkoxyquinazolin-4-one having the formula (6):

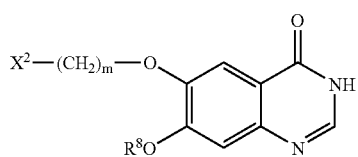

(6)

wherein $R^8$ and m have the same meaning as above, and $X^2$ represents a halogen atom, with an amine compound having the formula (23):

$$R^{10}\text{—}NH\text{—}R^{11} \quad (23)$$

wherein $R^{10}$ and $R^{11}$ have the dame meaning as above.

Furthermore, the invention resides in a new compound embraced in the aforementioned formula (24), namely, 6-methoxy-7-(3-thiomorpholinopropoxy)quinazolin-4-one having the formula (26):

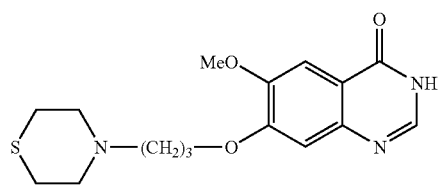

(26)

wherein Me is methyl.

DETAILED DESCRIPTION OF THE INVENTION

The anthranilic acid compound employed in the invention is represented by the aforementioned formula (1).

In the formula (1), each of $R^1$, $R^2$, $R^3$ and $R^4$ is the same or different, can have a substituent, and does not participate in the reaction. In more detail, each can be hydrogen, alkyl, cycloalkyl, aralkyl, aryl, halogen, hydroxyl, alkoxy, alkylthio, nitro, cyano, carbonyl, or amino (not for $R^1$). Otherwise, $R^1$, $R^2$, $R^3$ and $R^4$ may be combined to form a ring.

The alkyl group can contain 1 to 12 carbon atoms. Examples of the alkyl groups include methyl, ethyl, propyl, butyl, pentyl, hexyl, heptyl, octyl, nonyl, and decyl. These groups can be any of isomers.

The cycloalkyl group can contain 3 to 12 carbon atoms. Examples of the cycloalkyl groups include cyclopropyl, cyclobutyl, cyclopentyl, cyclohexyl, cycloheptyl, and cyclooctyl.

The aralkyl group can contain 7 to 14 carbon atoms. Examples of the aralkyl groups include benzyl, phenethyl, and phenylpropyl. These groups can be any of isomers.

The aryl group can contain 6 to 14 carbon atoms. Examples of the aryl groups include phenyl, p-tolyl, naphthyl, and anthranyl. These groups can be any of isomers.

Examples of halogen atoms include fluorine, chlorine, bromine, and iodine.

The alkoxy group can contain 1 to 12 carbon atoms. Examples of the alkoxy groups include methoxy, ethoxy, and propoxy. These groups can be any of isomers.

The alkylthio group can contain 1 to 12 carbon atoms. Examples of the alkylthio groups include methylthio, ethylthio, and propylthio. These groups can be any of isomers.

The above-mentioned alkyl, cycloalkyl, aralkyl, aryl, alkoxy, alkylthio, and amino(not for $R^1$) may have a substituent. Examples of the substituents include a substituent bonded via a carbon atom, a substituent bonded via an oxygen atom, a substituent bonded via a nitrogen atom, a substituent bonded via a sulfur atom, and a halogen atom.

Examples of the substituents bonded via a carbon atom include alkyl groups such as methyl, ethyl, propyl, butyl, pentyl, and hexyl; cycloalkyl groups such as cyclopropyl, cyclobutyl, cyclopentyl, and cyclohexyl; alkenyl groups such as vinyl, allyl, propenyl, cyclopropenyl, cyclobutenyl, and cyclopentenyl; heterocyclic alkenyl groups such as pyrrolidinyl, pyrrolyl, furyl, and thienyl; aryl groups such as phenyl, tolyl, xylyl, biphenylyl, naphthyl, anthryl, and phenanthoryl; acyl groups (may be acetallized) such as formyl, acetyl, propionyl, acryloyl, pivaloyl, cyclohexylcarbonyl, benzoyl, naphthoyl, and toluoyl; carboxyl groups; alkoxycarbonyl groups such as methoxycarbonyl and ethoxycarbonyl; aryloxycarbonyl groups such as phenoxycarbonyl; halogenated alkyl groups such as trifluoromethyl; and cyano group. These groups can be any of isomers.

Examples of the substituents bonded via an oxygen atom include hydroxyl; alkoxy groups such as methoxy, ethoxy, propoxy, butoxy, pentyloxy, hexyloxy, heptyloxy, and benzyloxy; and aryloxy groups such as phenoxy, toluyloxy, and naphthyloxy. These groups can be any of isomers.

Examples of the substituents bonded via a nitrogen atom include primary amino groups such as methylamino, ethylamino, butylamino, cyclohexylamino, phenylamino, and naphthylamino; secondary amino groups such as dimethylamino, diethylamino, dibutylamino, methylethylamino, methylbutylamino, and diphenylamino; heterocyclic amino groups such as morpholino, piperidino, piperazinyl, pyrazolidinyl, pyrrolidino, and indolyl; and imino group. These groups can be any of isomers.

Examples of the substituents bonded via a sulfur atom include mercapto; thioalkoxy groups such as thiomethoxy, thioethoxy, and thiopropoxy; and thioaryloxy groups such as thiophenoxy, thiotoluyloxy, and thionaphthyloxy. These groups can be any of isomers.

Examples of the halogen atoms include fluorine, chlorine, bromine, and iodine.

$R^5$ is a hydrogen atom or a hydrocarbyl group. Examples of the hydrocarbyl groups include alkyl groups such as methyl, ethyl, propyl, butyl, pentyl, and hexyl; cycloalkyl groups such as cyclopropyl, cyclobutyl, cyclopentyl, and cyclohexyl; aralkyl groups such as benzyl, phenethyl, and phenylpropyl; and aryl groups such as phenyl, tolyl, naphthyl, and anthryl. These groups can be any of isomers.

Examples of the formic acid derivatives employed in the reaction of converting a compound of the formula (1) to a compound of the formula (2) include formic acid, formic acid esters such as methyl formate and ethyl formate; and orthoformic acid esters such as methyl orthoformate and ethyl orthoformate. Preferred are formic acid esters and orthoformic acid esters. More preferred are orthoformic acid esters. Specifically preferred are methyl orthoformate and ethyl orthoformate.

The formic acid derivative can be employed preferably in an amount of 1.0 to 30 moles, more preferably 1.1 to 10 moles, per one mole of the anthranilic acid compound.

Examples of the ammonium carboxylates include ammonium aliphatic carboxylates such as ammonium formate, ammonium acetate, and ammonium propionate and ammonium aromatic carboxylates such as benzoate and dichlorobenzoate. Preferred are ammonium aliphatic carboxylate. More preferred are ammonium formate and ammonium acetate. A specifically preferred is ammonium acetate. These ammonium carboxylates can be employed singly or in combination.

The ammonium carboxylate can be employed preferably in an amount of 1.0 to 10.0 moles, more preferably 1.1 to 6.0 moles, per one mole of the anthranilic acid compound.

The above-mentioned reaction can be performed in the presence or absence of a solvent. There are no specific limitations with respect to the solvents, so far as the solvents do not participate in the reaction. Examples are alcohols such as methanol, ethanol, isopropyl alcohol, n-butyl alcohol, and t-butyl alcohol; amides such as N,N-dimethylformamide and N-methylpyrrolidone; ureas such as N,N'-dimethylimidazolidinone; sulfoxides such as dimethyl sulfoxide; aromatic hydrocarbons such as benzene, toluene, xylene, and mesitylene; halogenated aliphatic hydrocarbons such as methylene chloride, chloroform, and dichloroethane; nitrites such as acetonitrile and propionitrile; and ethers such as diethyl ether, tetrahydrofuran, and dioxane. Preferred are alcohols, amides, and nitrites. More preferred are methanol, ethanol, N,N'-dimethylimidazolidinone, and acetonitrile. These solvents can be employed singly or in combination.

The amount of the solvent employed in the reaction depends on the homogeneity and stirring condition of the reaction mixture. It is preferred that the solvent is employed in an amount of 0 to 50 g (more preferably 0 to 20 g, most preferably 0 to 5 g) per one gram of the anthranilic acid compound.

The reaction of the invention can be performed, for instance, by mixing and stirring an ammonium carboxylate, an anthranilic acid compound, an formic acid derivative, and a solvent in an inert gas atmosphere. The reaction is preferably performed at a temperature of 40 to 200° C., more preferably 50 to 150° C. There is no limitation with respect to the pressure for the reaction.

After the reaction is complete, the final product, i.e., a quinazolin-4-one compound, can be isolated and purified by the conventional procedures such as extraction, filtration, concentration, distillation, recrystallization, and column chromatography.

In the 5-alkoxy-4-halogenoalkoxyanthranilic acid compound or 4-alkoxy-5-halogenoalkoxyanthranilic acid compound which is employed in the reaction of converting a compound of the formula (3) to a compound of the formula (4) or the reaction of converting a compound of the formula (5) to a compound of the formula (6), each of $R^6$ and $R^8$ is an alkoxy group. Examples are alkyl groups having 1 to 12 carbon atoms such as methyl, ethyl, propyl, butyl, pentyl, and hexyl. These groups can be any of isomers.

Each of $R^7$ and $R^9$ is a hydrogen atom or a hydrocarbyl group. Examples of the hydrocarbyl groups include alkyl groups having 1 to 12 carbon atoms such as methyl, ethyl, propyl, butyl, pentyl, and hexyl; cycloalkyl groups having 3 to 12 carbon atoms such as cyclopropyl, cyclobutyl, cyclopentyl, and cyclohexyl; aralkyl groups having 7 to 14 carbon atoms such as benzyl, phenethyl, and phenylpropyl; and aryl groups having 6 to 14 carbon atoms such as phenyl, tolyl, naphthyl, and anthryl. These groups can be any of isomers.

Each of $X^1$ and $X^2$ is a halogen atom. Examples of the halogen atoms include fluorine, chlorine, bromine, and iodine.

Each of n and m is an integer of 2 to 4.

Examples of the formic acid derivatives employed in the above-mentioned reaction include formic acid, formic acid esters such as methyl formate and ethyl formate; and orthoformic acid esters such as methyl orthoformate and ethyl orthoformate. Preferred are formic acid esters and orthoformic acid esters. More preferred are orthoformic acid esters. Specifically preferred are methyl orthoformate and ethyl orthoformate.

The formic acid derivative can be employed preferably in an amount of 1.0 to 30 moles, more preferably 1.1 to 10 moles, per one mole of the 5-alkoxy-4-halogeno-alkoxyanthranilic acid compound or 4-alkoxy-5-halogeno-alkoxyanthranilic acid compound.

Examples of the ammonium carboxylates employed in the above-mentioned reaction include ammonium aliphatic carboxylates such as ammonium formate, ammonium acetate, and ammonium propionate and ammonium aromatic carboxylates such as benzoate and dichlorobenzoate. Preferred are ammonium aliphatic carboxylate. More preferred are ammonium formate and ammonium acetate. A specifically preferred is ammonium acetate. The ammonium carboxylates can be employed singly or in combination.

The ammonium carboxylate can be employed preferably in an amount of 1.0 to 10.0 moles, more preferably 1.1 to 6.0 moles, per one mole of the 5-alkoxy-4-halogenoalkoxy-anthranilic acid compound or 4-alkoxy-5-halogenoalkoxy-anthranilic acid compound.

The above-mentioned reaction can be performed in the presence or absence of a solvent. There are no specific limitations with respect to the solvents, so far as the solvents do not participate in the reaction. Examples are alcohols such as methanol, ethanol, isopropyl alcohol, n-butyl alcohol, and t-butyl alcohol; amides such as N,N-dimethylformamide and N-methylpyrrolidone; ureas such as N,N'-dimethylimidazolidinone; sulfoxides such as dimethyl sulfoxide; aromatic hydrocarbons such as benzene, toluene, xylene, and mesitylene; halogenated aliphatic hydrocarbons such as methylene chloride, chloroform, and dichloroethane; nitrites such as acetonitrile and propionitrile; and ethers such as diethyl ether, tetrahydrofuran, and dioxane. Preferred are alcohols, amides, and nitrites. More preferred are methanol, ethanol, N,N'-dimethylimidazolidinone, and acetonitrile. The solvents can be employed singly or in combination.

The amount of the solvent employed in the reaction depends on the homogeneity and stirring condition of the reaction mixture. It is preferred that the solvent is employed in an amount of 0 to 50 g (more preferably 0 to 20 g, most preferably 0 to 5 g) per one gram of the 5-alkoxy-4-halogenoalkoxyanthranilic acid compound or 4-alkoxy-5-halogenoalkoxyanthranilic acid compound.

The reaction of the invention can be performed, for instance, by mixing and stirring an ammonium carboxylate, an anthranilic acid compound, an formic acid derivative, and a solvent in an inert gas atmosphere. The reaction is preferably performed at a temperature of 40 to 200° C., more preferably 50 to 150° C. There is no limitation with respect to the pressure for the reaction.

After the reaction is complete, the final product, i.e., the 5-alkoxy-4-halogenoalkoxyanthranilic acid compound or 4-alkoxy-5-halogenoalkoxyanthranilic acid compound, can be isolated and purified by the conventional procedures such as extraction, filtration, concentration, distillation, recrystallization, and column chromatography.

In the 5-alkoxy-4-halogenoalkoxy-2-nitrobenzoic acid compound or 4-alkoxy-5-halogenoalkoxy-2-nitrobenzoic acid compound which is employed in the reaction of converting a compound of the formula (9) to a compound of the formula (3) or the reaction of converting a compound of the formula (10) to a compound of the formula (5), each of $R^6$ and $R^8$ is an alkoxy group. Examples are alkyl groups having 1 to 12 carbon atoms such as methyl, ethyl, propyl, butyl, pentyl, and hexyl. These groups can be any of isomers.

Each of $R^7$ and $R^9$ is a hydrogen atom or a hydrocarbyl group. Examples of the hydrocarbyl groups include alkyl groups having 1 to 12 carbon atoms such as methyl, ethyl, propyl, butyl, pentyl, and hexyl; cycloalkyl groups having 3 to 12 carbon atoms such as cyclopropyl, cyclobutyl, cyclopentyl, and cyclohexyl; aralkyl groups having 7 to 14 carbon atoms such as benzyl, phenethyl, and phenylpropyl; and aryl groups having 6 to 14 carbon atoms such as phenyl, tolyl, naphthyl, and anthryl. These groups can be any of isomers.

Each of $X^1$ and $X^2$ is a halogen atom. Examples of the halogen atoms include fluorine, chlorine, bromine, and iodine.

Each of n and m is an integer of 2 to 4.

There are no specific limitation with respect to the above-mentioned reducing reaction, so long as the reaction can convert the nitro group directly attached to the aromatic compound into an amino group. The reaction is preferably performed in the presence of a metallic catalyst, in a hydrogen atmosphere, or in the presence of formic acid.

The metallic catalyst contains palladium, platinum, or nickel. Examples are palladium/carbon, palladium/barium sulfate, palladium hydroxide/carbon, platinum/carbon, platinum sulfide/carbon, palladium-platinum/carbon, platinum oxide, and Raney-nickel. Preferred are palladium/carbon, platinum sulfide/carbon, and Raney-nickel. The metallic catalyst can be employed singly or in combination.

The metallic catalyst can be employed preferably in an amount of 0.1 to 1,000 mg, more preferably 5 to 500 mg, per one gram of the 5-alkoxy-4-halogenoalkoxy-2-nitrobenzoic acid compound or 4-alkoxy-5-halogenoalkoxy-2-nitrobenzoic acid compound.

The hydrogen can be employed preferably in an amount of 3 to 50 moles, more preferably 3 to 10 moles, per one mole of the 5-alkoxy-4-halogenoalkoxy-2-nitrobenzoic acid compound or 4-alkoxy-5-halogenoalkoxy-2-nitrobenzoic acid compound.

The formic acid can be employed preferably in an amount of 1 to 100 g, more preferably 5 to 50 g, per one gram of the 5-alkoxy-4-halogenoalkoxy-2-nitrobenzoic acid compound or 4-alkoxy-5-halogenoalkoxy-2-nitrobenzoic acid compound.

The above-mentioned reaction is preferably performed in the presence of a solvent. There are no specific limitations with respect to the solvents, so far as the solvents do not participate in the reaction. Examples are alcohols such as methanol, ethanol, isopropyl alcohol, n-butyl alcohol, and t-butyl alcohol; carboxylic acid esters such as methyl acetate, ethyl acetate, and methyl propionate; aromatic hydrocarbons such as benzene, toluene, xylene, and mesitylene; and ethers such as diethyl ether, tetrahydrofuran, and dioxane. Preferred are alcohols and carboxylic acid ester. More preferred are methanol, ethanol, and ethyl acetate. These solvents can be employed singly or in combination.

The amount of the solvent employed in the reaction depends on the homogeneity and stirring condition of the reaction mixture. It is preferred that the solvent is employed in an amount of 1 to 100 g (more preferably 3 to 30 g) per one gram of the 5-alkoxy-4-halogenoalkoxy-2-nitrobenzoic acid compound or 4-alkoxy-5-halogenoalkoxy-2-nitrobenzoic acid compound.

The above-mentioned reaction can be performed by mixing and stirring the 5-alkoxy-4-halogenoalkoxy-2-nitrobenzoic acid compound or 4-alkoxy-5-halogenoalkoxy-2-nitrobenzoic acid compound, a metallic catalyst, and a solvent in the presence of a hydrogen gas (which can be diluted with an inert gas) or formic acid. The reaction temperature preferably is 0 to 300° C., more preferably 20 to 200° C. The reaction pressure preferably is 0.1 to 10 MPa, more preferably 0.1 to 2 MPa.

The reducing reaction can be performed after addition of an acid or an active carbon, so that the reactivity can be enhanced. The acid can be an inorganic acid such as hydrochloric acid, nitric acid, sulfuric acid, or phosphoric acid, or an organic acid such as formic acid, acetic acid, or propionic acid. Preferred is an organic acid. Most preferred is acetic acid. These acids can be employed singly or in combination. The acid and active carbon can be employed in combination.

It is preferred that the acid is employed in an amount of 0.01 to 20 moles (more preferably 0.1 to 5.0 moles) per one mole of the 5-alkoxy-4-halogenoalkoxy-2-nitrobenzoic acid compound or 4-alkoxy-5-halogenoalkoxy-2-nitrobenzoic acid compound.

It is preferred that the active carbon is employed in an amount of 0.01 to 10 g (more preferably 0.1 to 5.0 g) per one gram of the 5-alkoxy-4-halogenoalkoxy-2-nitrobenzoic acid compound or 4-alkoxy-5-halogenoalkoxy-2-nitrobenzoic acid compound.

After the reaction is complete, the final product, i.e., the 5-alkoxy-4-halogenoalkoxyanthranilic acid compound or 4-alkoxy-5-halogenoalkoxyanthranilic acid compound, can be isolated and purified by the conventional procedures such as filtration, concentration, distillation, recrystallization, crystallization, and column chromatography.

In the following, the process for preparing a compound of the formula (9) or (10) from a compound of the formula (15) or (18), respectively, is described.

The process consists of a first step for converting a compound of the formula (15) or (18) to a compound of the formula (17) or (20), respectively, and a second step for converting the compound of the formula (17) or (20) to a compound of the formula (9) or (10), respectively.

The first and second steps are sequentially described below.

(A) First Step

In the first step, the 3-alkoxy-4-hydroxybenzoic acid compound or 4-alkoxy-3-hydroxybenzoic acid compound is reacted with a dihalogenoalkane in an organic solvent, to give a 3-alkoxy-4-halogenoalkoxybenzoic acid compound or 4-alkoxy-3-halogenoalkoxybenzoic acid compound, respectively.

The 3-alkoxy-4-hydroxybenzoic acid compound or 4-alkoxy-3-hydroxybenzoic acid compound employed in the first step is represented by the aforementioned formula (15) or (18), respectively. In the formula (15) or (18), each of $R^6$ and $R^8$ is an alkyl group having 1 to 12 carbon atoms. Examples are methyl, ethyl, propyl, butyl, pentyl, and hexyl. These groups can be any of isomers.

Each of $R^7$ and $R^9$ is a hydrogen atom or a hydrocarbyl group. Examples of the hydrocarbyl groups include alkyl groups having 1 to 12 carbon atoms such as methyl, ethyl, propyl, butyl, pentyl, and hexyl; cycloalkyl groups having 3 to 12 carbon atoms such as cyclopropyl, cyclobutyl, cyclopentyl, and cyclohexyl; aralkyl groups having 7 to 14 carbon atoms such as benzyl, phenethyl, and phenylpropyl; and aryl groups having 6 to 14 carbon atoms such as phenyl, tolyl, naphthyl, and anthryl. These groups can be any of isomers.

In the first step, a dihalogenoalkane of the aforementioned formula (16) or (19) is employed. In the formula (16) or (19), each of $X^3$, $X^4$, $X^5$, and $X^6$ is a halogen atom. Examples are fluorine, chlorine, bromine, and iodine.

Each of n and m is an integer of 2 to 4.

The dihalogenoalkane is employed preferably in an amount of 1.0 to 100 moles, more preferably 1.1 to 50 moles, particularly preferably 1.1 to 15 moles, per one mole of the 3-alkoxy-4-hydroxybenzoic acid compound or 4-alkoxy-3-hydroxybenzoic acid compound.

The base employed in the first step can be an alkali metal hydroxide such as sodium hydroxide or potassium hydroxide, an alkali metal carbonate such as sodium carbonate or potassium carbonate, an alkali metal hydrogen carbonate such as sodium hydrogen carbonate or potassium hydrogen carbonate, and an alkali metal alkoxide such as sodium methoxide or potassium methoxide. Preferred are an alkali metal hydroxide and an alkali metal carbonate.

More preferred is an alkali metal carbonate. Particularly preferred is potassium carbonate. These bases can be employed singly or in combination.

The base is employed preferably in an amount of 1.0 to 2.9 moles, more preferably 1.1 to 2.5 moles, particularly preferably 1.1 to 2.0 moles, per one mole of the 3-alkoxy-4-hydroxybenzoic acid compound or 4-alkoxy-3-hydroxybenzoic acid compound.

There are no specific limitations with respect to the solvent employed in the first step, so far as the solvent does not participate in the reaction. Examples are alcohols such as methanol, ethanol, isopropyl alcohol, n-butyl alcohol, and t-butyl alcohol; ketones such as acetone, methyl ethyl ketone, and methyl isopropyl ketone; amides such as N,N-dimethylformamide and N-methylpyrrolidone; ureas such as N,N'-dimethylimidazolidinone; sulfoxides such as dimethyl sulfoxide; nitriles such as acetonitrile and propionitrile; ethers such as diethyl ether, diisopropyl ether, tetrahydrofuran, and dioxane; and aromatic hydrocarbons such as toluene and xylene. Preferred are ketones and nitriles. These solvents can be employed singly or in combination.

The amount of the solvent employed in the reaction depends on the homogeneity and stirring condition of the reaction mixture. It is preferred that the solvent is employed in an amount of 1 to 100 g (more preferably 5 to 50 g) per one gram of the 3-alkoxy-4-hydroxybenzoic acid compound or 4-alkoxy-3-hydroxybenzoic acid compound.

The first step can be performed by mixing and stirring the 3-alkoxy-4-hydroxybenzoic acid compound or 4-alkoxy-3-hydroxybenzoic acid compound, dihalogenoalkane, base, and organic solvent in an inert gas atmosphere.

The reaction is preferably performed at a temperature of 20 to 200° C., more preferably 40 to 120° C. There is no limitation with respect to the pressure for the reaction.

In the first step, a metal chloride such as sodium chloride, potassium chloride, or calcium chloride (preferably, an alkali metal chloride or an alkaline earth metal chloride) can be placed in the reaction system to reduce production of side-products (e.g., 1,3-bis(2-methoxy-4-methoxycarbonylphenoxy)propane). The metal chlorides can be employed singly or in combination.

The metal chloride can be employed preferably in an amount of 0.1 to 20 moles, more preferably 0.5 to 10 moles, per one mole of the 3-alkoxy-4-hydroxybenzoic acid compound or 4-alkoxy-3-hydroxybenzoic acid compound.

After the reaction is complete, the final product in the first step, i.e., the 3-alkoxy-4-halogenoalkoxybenzoic acid compound or 4-alkoxy-3-halogenoalkoxybenzoic acid compound, can be isolated and purified by the conventional procedures such as filtration, concentration, distillation, recrystallization, crystallization, and column chromatography, and the isolated and purified product can be then employed in the second step. Otherwise, the product in the first step can be employed in the second step without it is isolated and purified.

In the first step, a 3-alkoxy-4-halogenoalkoxybenzoic acid compound of the formula (17) or a 4-alkoxy-3-halogenoalkoxybenzoic acid compound of the formula (2) is obtained. In the formulas (17) and (20), $R^6$, $R^7$, $R^8$, $R^9$, n, and m have the same meaning as defined hereinbefore, $X^1$ is the same as $X^3$ or $X^4$, and $X^2$ is the same as $X^5$ or $X^6$.

(B) Second Step

In the second step, the 3-alkoxy-4-halogenoalkoxybenzoic acid compound or a 4-alkoxy-3-halogenoalkoxybenzoic acid compound is reacted and nitrated by nitric acid in the presence of an alkali metal nitrite, to give a 5-alkoxy-4-halogenoalkoxy-2-nitrobenzoic acid compound or a 4-alkoxy-5-halogenoalkoxy-2-nitrobenzoic acid compound, respectively.

The nitric acid is employed preferably in an amount of 1.0 to 50 moles, more preferably 3.0 to 10 moles, per one mole of the 3-alkoxy-4-halogenoalkoxybenzoic acid compound or 4-alkoxy-3-halogenobenzoic acid compound. The concentration of nitric acid preferably is 40 to 80 wt. %, more preferably 50 to 70 wt. %.

The alkali metal nitrite employed in the second step can be sodium nitrite and potassium nitrite. Preferred is sodium nitrite.

The alkali metal nitrite is employed preferably in an amount of 0.001 to 1 mole, more preferably 0.01 to 0.5 mole, per one mole of the 3-alkoxy-4-halogenoalkoxybenzoic acid compound or 4-alkoxy-3-halogenobenzoic acid compound.

The second step can be preferably performed in the presence of a solvent. There are no specific limitations with respect to the solvent, so far as the solvent does not participate in the reaction. Examples are carboxylic acids such as formic acid, acetic acid, propionic acid, and butyric acid. Preferred is acetic acid. The solvents can be employed singly or in combination.

The amount of the solvent depends on the homogeneity and stirring condition of the reaction mixture. It is preferred that the solvent is employed in an amount of 1 to 50 g (more preferably 1.1 to 20 g) per one gram of the 3-alkoxy-4-halogenoalkoxybenzoic acid compound or 4-alkoxy-3-halogenobenzoic acid compound.

After the reaction is complete, the final product in the second step, i.e., the 5-alkoxy-4-halogenoalkoxy-2-nitrobenzoic acid compound or 4-alkoxy-5-halogenoalkoxy-2-nitrobenzoic acid compound, can be isolated and purified by the conventional procedures such as filtration, concentration, distillation, recrystallization, crystallization, and column chromatography.

A 6-alkoxy-7-halogenoalkoxyquinazolin-4-one of the aforementioned formula (4) and a 7-alkoxy-6-halogenoalkoxyquinazolin-4-one of the aforementioned formula (6) can be readily converted, respectively, to a 6-alkoxy-7-aminoalkoxyquinazolin-4-one of the formula (24) and a 7-alkoxy-6-aminoalkoxyquinazolin-4-one of the formula (25) by the below-mentioned process. In each formula, $R^6$ is an alkyl group having 1 to 12 carbon atoms, such as methyl, ethyl, propyl, butyl, pentyl, or hexyl. These groups can be any of isomers.

Each of $X^1$ and $X^2$ is a halogen atom. Examples are fluorine, chlorine, bromine, and iodine.

Each of n and m is an integer of 2 to 4.

In the above-mentioned reaction, an amine compound is employed. The amine compound is represented by the aforementioned formula (23). In the formula (23), each of $R^{10}$ and $R^{11}$ is a hydrogen atom or a hydrocarbyl group which can contain a hetero atom. Examples are alkyl groups having 1 to 12 carbon atoms such as methyl, ethyl, propyl, butyl, pentyl, and hexyl; cycloalkyl groups having 3 to 12 carbon atoms such as cyclopropyl, cyclobutyl, cyclopentyl, and cyclohexyl; aralkyl groups having 7 to 14 carbon atoms such as benzyl, phenethyl, and phenylpropyl; and aryl groups having 6 to 14 carbon atoms such as phenyl, tolyl, naphthyl, and anthryl. These groups can be any of isomers.

$R^{10}$ and $R^{11}$ can be combined to form a ring (including a heterocyclic ring). Examples of groups which can produce a ring (including a heterocyclic ring) in combination pentamethylene, 1-methylpentamethylene, 3-methylpentamethylene, 3-oxypentamethylene, and 3-thiopentamethylene.

The amine compound is employed preferably in an amount of 1.0 to 100 moles, more preferably 1.1 to 10 moles, per one mole of the 6-alkoxy-7-halogenoalkoxyquinazolin-4-one or 7-alkoxy-3-halogenoalkoxyquinazolin-4-one.

The above-mentioned reaction can be performed in the presence or absence of a solvent. There are no specific limitations with respect to the solvents, so far as the solvents do not participate in the reaction. Examples are water, alcohols such as methanol, ethanol, isopropyl alcohol, n-butyl alcohol, sec-butyl alcohol, and t-butyl alcohol; amides such as N,N-dimethylformamide and N-methylpyrrolidone; ureas such as N,N'-dimethylimidazolidinone; sulfoxides such as dimethyl sulfoxide; aromatic hydrocarbons such as benzene, toluene, xylene, and mesitylene; halogenated aliphatic hydrocarbons such as methylene chloride, chloroform, and dichloroethane; nitrites such as acetonitrile and propionitrile; ethers such as diethyl ether, tetrahydrofuran, and dioxane; and ketones such as acetone, methyl ethyl ketone, and diethyl ketone. Preferred are water and alcohols. More preferred are water, methanol, ethanol, and sec-butyl alcohol. These solvents can be employed singly or in combination.

The amount of the solvent employed in the reaction depends on the homogeneity and stirring condition of the reaction mixture. It is preferred that the solvent is employed in an amount of 0 to 50 g (more preferably 0 to 20 g) per one gram of the 6-alkoxy-7-halogenoalkoxyquinazolin-4-one or 7-alkoxy-6-halogenoalkoxyquinazolin-4-one.

The above-mentioned reaction can be performed in the presence or absence of a base. The base can be an alkali metal hydroxide such as lithium hydroxide, sodium hydroxide, or potassium hydroxide, an alkali metal carbonate such as lithium carbonate, sodium carbonate, or potassium carbonate, an alkali metal hydrogen carbonate such as lithium hydrogen carbonate, sodium hydrogen carbonate, or potassium hydrogen carbonate, an alkali metal phosphate such as sodium phosphate or potassium phosphate, an alkali metal carboxylate such as sodium acetate, potassium acetate, sodium propionate, or potassium propionate, an alkali metal alkoxide such as sodium methoxide, potassium methoxide, sodium ethoxide, potassium ethoxide, potassium t-butoxide, a tertiary amine such as trimethylamine, triethylamine, ethyldiisopropylamine, diethylisopropylamine, triisopropylamine, benzyldimethylamine, or benzyldiethylamine, and a pyridine compound such as pyridine, methylpyridine, or dimethylpyridine. Preferred are an alkali metal hydroxide and an alkali metal carbonate. More preferred is sodium hydroxide, potassium hydroxide, sodium carbonate, and potassium carbonate. These bases can be employed singly or in combination.

The base is employed preferably in an amount of 0 to 20 moles, more preferably 0 to 10 moles, per one mole of the 6-alkoxy-7-halogenoalkoxyquinazolin-4-one or 7-alkoxy-6-halogenoalkoxyquinazolin-4-one.

The above-mentioned reaction can be performed, for instance, by mixing and stirring the 6-alkoxy-7-halogenoalkoxyquinazolin-4-one or 7-alkoxy-6-halogenoalkoxyquinazolin-4-one, an amino compound and a solvent in an inert gas atmosphere. The reaction is preferably performed at a temperature of 20 to 200° C., more preferably 40 to 150° C. There is no limitation with respect to the pressure for the reaction.

After the reaction is complete, the final product, i.e., 6-alkoxy-7-aminoalkoxyquinazolin-4-one and 7-alkoxy-6-aminoalkoxyquinazolin-4-one, can be isolated and purified by the conventional procedures such as filtration, concentration, distillation, recrystallization, and column chromatography.

The invention is further described by the following examples.

Example I-1

Preparation of 6-iodoquinazolin-4-one

In a 10-mL volume stainless steel pressure-resistant vessel were placed 1.0 g (3.8 mmol) of 5-iodoanthranilic acid, 0.81 g (7.6 mmol) of methyl orthoformate, 0.59 g (7.6 mmol) of ammonium acetate, and 4.0 mL of methanol. The reaction was carried out at 120° C. for 3 hours. After the reaction was complete, the reaction mixture was cooled to room temperature, and 40 mL of water was added to the reaction mixture. The resulting aqueous mixture was stirred for 15 minutes and filtered to give 0.97 g (isolated yield: 93%) of 6-iodoquinazolin-4-one as a pale gray crystalline product.

6-Iodoquinazolin-4-one had the following characteristics.
m.p.: 259° C. (decomp.)
$^1$H-NMR (DMSO-$d_6$, δ (ppm)): 7.46 (1H, d, J=8.4 Hz) 8.08-8.15 (2H, m), 8.39 (1H, d, J=1.8 Hz), 12.5 (1H, brs)
CI-MS (m/e): 273 (M+1)

Example I-2

Preparation of 6-iodoquinazolin-4-one

The procedures of Example I-1 were repeated except that the amounts of methyl orthoformate and ammonium acetate were changed to 1.61 g (15.2 mmol) and 1.17 g (15.2 mmol), respectively. There was obtained 0.98 g (reaction yield: 94%) of 6-iodoquinazolin-4-one.

Example I-3

Preparation of 6-iodoquinazolin-4-one

The procedures of Example I-2 were repeated except that the amount of methyl orthoformate was changed to 3.60 g (34 mmol) and that no methanol was used. There was obtained 0.94 g (reaction yield: 91%) of 6-iodoquinazolin-4-one.

Example I-4

Preparation of 6-iodoquinazolin-4-one

The procedures of Example I-2 were repeated except that methanol was replaced with acetonitrile. There was obtained 0.98 g (reaction yield: 94%) of 6-iodoquinazolin-4-one.

Example I-5

Preparation of 6-iodoquinazolin-4-one

The procedures of Example I-2 were repeated except that ammonium acetate was replaced with 3.20 g (15.2 mmol) of ammonium 2,4-dichlorobenzoate. There was obtained 0.97 g (reaction yield: 90%) of 6-iodoquinazolin-4-one.

Example I-6

Preparation of 6-iodoquinazolin-4-one

The procedures of Example I-2 were repeated except that ammonium acetate was replaced with 0.95 g (15.2 mmol) of ammonium formate. After the reaction was complete, the reaction mixture was treated in the manner of Example I-1. There was obtained 0.88 g (isolated yield: 85%) of 6-iodoquinazolin-4-one as a pale gray crystalline product.

Example I-7

Preparation of 7-chloroquinazolin-4-one

In a 10-mL volume stainless steel pressure-resistant vessel were placed 1.00 g (5.8 mmol) of 4-chloroanthranilic acid, 2.47 g (23.3 mmol) of methyl orthoformate, 1.80 g (23.3 mmol) of ammonium acetate, and 4.0 mL of methanol. The reaction was carried out at 120° C. for 3 hours. After the reaction was complete, the reaction mixture was cooled to room temperature, and 40 mL of water was added to the reaction mixture. The resulting aqueous mixture was stirred for 15 minutes and filtered to give 0.96 g (isolated yield: 92%) of 7-chloroquinazolin-4-one as a white crystalline product.

7-Chloroquinazolin-4-one had the following characteristics.

m.p.: 246-247° C.
$^1$H-NMR (DMSO-$d_6$, δ (ppm)): 7.56 (1H, dd, J=1.8, 8.1 Hz), 7.72 (1H, d, J=1.8 Hz), 8.10-8.14 (2H, m), 12.5 (1H, brs)
CI-MS (m/e): 181 (M+1)

Example I-8

Preparation of 6-nitroquinazolin-4-one

In a 10-mL volume stainless steel pressure-resistant vessel were placed 1.00 g (5.5 mmol) of 6-nitroanthranilic acid, 2.33 g (22.0 mmol) of methyl orthoformate, 1.69 g (22.0 mmol) of ammonium acetate, and 4.0 mL of methanol. The reaction was carried out at 120° C. for 3 hours. After the reaction was complete, the reaction mixture was cooled to room temperature, and 40 mL of water was added to the reaction mixture. The resulting aqueous mixture was stirred for 15 minutes and filtered to give 0.91 g (isolated yield: 87%) of 6-nitroquinazolin-4-one as a yellow crystalline product.

6-Nitroquinazolin-4-one had the following characteristics.

m.p.: 277-278° C.
$^1$H-NMR (DMSO-$d_6$, δ (ppm)): 7.87 (1H, d, J=9.0 Hz), 8.32 (1H, s), 8.55 (1H, dd, J=2.7, 9.0 Hz), 8.81 (1H, d, J=2.7 Hz), 12.5 (1H, brs)
CI-MS (m/e): 192 (M+1)

Example I-9

Preparation of 6,7-dimethoxyquinazolin-4-one

In a 10-mL volume stainless steel pressure-resistant vessel were placed 1.00 g (5.1 mmol) of 4,5-dimethoxyanthranilic acid, 2.15 g (20.3 mmol) of methyl orthoformate, 1.56 g (20.3 mmol) of ammonium acetate, and 4.0 mL of methanol. The reaction was carried out at 120° C. for 3 hours. After the reaction was complete, the reaction mixture was cooled to room temperature, and 40 mL of water was added to the reaction mixture. The resulting aqueous mixture was stirred for 15 minutes and filtered to give 0.96 g (isolated yield: 92%) of 6,7-dimethoxyquinazolin-4-one as a brown crystalline product.

6,7-Dimethoxyquinazolin-4-one had the following characteristics.

m.p.: 294-295° C.
$^1$H-NMR (DMSO-$d_6$, δ (ppm)): 3.87 (3H, s), 3.90 (3H, s), 7.13 (1H, s), 7.44 (1H, s), 7.99 (1H, s), 12.5 (1H, brs)
CI-MS (m/e): 207 (M+1)

Example I-10

Preparation of 6-nitro-7-chloroquinazolin-4-one

In a 10-mL volume stainless steel pressure-resistant vessel were placed 0.94 g (4.3 mmol) of 4-chloro-5-nitroanthranilic acid, 1.96 g (18.5 mmol) of methyl orthoformate, 1.42 g (18.5 mmol) of ammonium acetate, and 4.0 mL of methanol. The reaction was carried out at 120° C. for 4 hours. After the reaction was complete, the reaction mixture was cooled to room temperature, and 40 mL of water was added to the reaction mixture. The resulting aqueous mixture was stirred for 15 minutes and filtered to give 0.88 g (isolated yield: 90%) of 6-nitro-7-chloroquinazolin-4-one as a yellow crystalline product.

6-Nitro-7-chloroquinazolin-4-one had the following characteristics.

m.p.: 300° C. (decomp.)
$^1$H-NMR (DMSO-$d_6$, δ (ppm)): 8.03 (1H, s), 8.32 (1H, s), 8.69 (1H, s), 12.5 (1H, brs)
CI-MS (m/e): 226 (M+1)

Example I-11

Preparation of 6-hydroxyquinazolin-4-one

In a 10-mL volume stainless steel pressure-resistant vessel were placed 1.00 g (6.6 mmol) of 5-hydroxyanthranilic acid, 2.80 g (26.4 mmol) of methyl orthoformate, 2.00 g (26.4 mmol) of ammonium acetate, and 4.0 mL of methanol. The reaction was carried out at 120° C. for 3 hours. After the reaction was complete, the reaction mixture was cooled to room temperature, and 40 mL of water was added to the reaction mixture. The resulting aqueous mixture was stirred for 15 minutes and filtered to give 0.78 g (isolated yield: 74%) of 6-hydroxyquinazolin-4-one as a pale gray crystalline product.

6-Hydroxyquinazolin-4-one had the following characteristics.

m.p.: 332-333° C. (decomp.)

$^1$H-NMR (DMSO-$d_6$, δ (ppm)): 7.25 (1H, dd, J=2.7, 8.7 Hz), 7.41 (1H, d, J=2.7 Hz), 7.53 (1H, d, J=8.7 Hz), 7.90 (1H, s), 12.0 (2H, brs)

CI-MS (m/e): 163 (M+1)

Example I-12

Preparation of 6-carboxyquinazolin-4-one

In a 10-mL volume stainless steel pressure-resistant vessel were placed 1.00 g (5.5 mmol) of 5-carboxyanthranilic acid, 2.30 g (22.0 mmol) of methyl orthoformate, 1.70 g (22.0 mmol) of ammonium acetate, and 4.0 mL of methanol. The reaction was carried out at 120° C. for 3 hours. After the reaction was complete, the reaction mixture was cooled to room temperature, and 40 mL of water and 10 mL of hydrochloric acid (1 mol/L) were added to the reaction mixture. The resulting aqueous mixture was stirred for 15 minutes and filtered to give 0.96 g (isolated yield: 84%, purity: 91% in terms of area percentage determined by high performance liquid chromatography) of 6-carboxyquinazolin-4-one as a yellow crystalline product.

6-Carboxyquinazolin-4-one had the following characteristics.

$^1$H-NMR (DMSO-$d_6$, δ (ppm)): 3.93 (1H, brs), 8.01 (1H, dd, J=1.5, 7.8 Hz), 8.17 (1H, d, J=1.5 Hz), 8.22 (1H, d, J=7.8 Hz), 8.28 (1H, s), 12.0 (2H, brs)

CI-MS (m/e): 191 (M+1)

Example I-13

Preparation of quinazolin-4-one

In a 2-mL volume stainless steel pressure-resistant vessel were placed 302 mg (2.0 mmol) of methyl anthranilate, 424 mg (4.0 mmol) of methyl orthoformate, 308 mg (4.0 mmol) of ammonium acetate, and 1.0 mL of methanol. The reaction was carried out at 120° C. for 3 hours. After the reaction was complete, the reaction mixture was analyzed (according to absolute quantitative analysis) by high performance liquid chromatography. There was produced 285 mg (reaction yield: 98%) of quinazolin-4-one.

Example I-14

Preparation of quinazolin-4-one

The procedures of Example I-13 were repeated except for replacing methanol with acetonitrile, to give 277 mg (reaction yield: 95%) of quinazolin-4-one.

Example I-15

Preparation of quinazolin-4-one

The procedures of Example I-13 were repeated except for replacing methanol with N,N'-dimethylimidazolidinone, to give 267 mg (reaction yield: 91%) of quinazolin-4-one.

Example I-16

Preparation of 6-nitro-7-(3-hydroxypropoxy)quinazolin-4-one

In a 10-mL volume stainless steel pressure-resistant vessel were placed 0.65 g (2.5 mmol) of 5-nitro-4-(3-hydroxypropoxy)anthranilic acid, 1.06 g (10.0 mmol) of methyl orthoformate, 0.77 g (10.0 mmol) of ammonium acetate, and 6.0 mL of methanol. The reaction was carried out at 140° C. for 6.5 hours. After the reaction was complete, the reaction mixture was cooled to room temperature, and 50 mL of water was added to the reaction mixture. The precipitated crystalline product was collected by filtration and dried under reduced pressure to give 0.52 g (isolated yield: 79%) of 6-nitro-7-(3-hydroxypropoxy)quinazolin-4-one as a gray crystalline product.

6-Nitro-7-(3-hydroxypropoxy)quinazolin-4-one had the following characteristics.

$^1$H-NMR (DMSO-$d_6$, δ (ppm)): 1.86-1.95 (2H, m), 3.57 (2H, t, J=6.0 Hz), 4.34 (2H, t, J=6.0 Hz), 7.42 (1H, s), 8.22 (1H, s), 8.53 (1H, s)

CI-MS (m/e): 266 (M+1)

Example I-17

Preparation of 6-nitro-7-hydroxyquinazolin-4-one

In a 10-mL volume stainless steel pressure-resistant vessel were placed 0.50 g (7.5 mmol) of 5-nitro-4-hydroxyanthranilic acid, 0.80 g (7.5 mmol) of methyl orthoformate, 0.58 g (7.5 mmol) of ammonium acetate, and 5.0 mL of methanol. The reaction was carried out at 120° C. for 3 hours. After the reaction was complete, the reaction mixture was cooled to room temperature, and methanol was distilled off under reduced pressure. Then, 5 mL of water was added to the reaction mixture. The precipitated crystalline product was collected by filtration and dried under reduced pressure to give 0.29 g (isolated yield: 55%) of 6-nitro-7-hydroxyquinazolin-4-one as a yellow crystalline product.

6-Nitro-7-hydroxyquinazolin-4-one had the following characteristics.

$^1$H-NMR (DMSO-$d_6$, δ (ppm)): 3.38 (1H, brs), 7.20 (1H, s), 8.15 (1H, s), 8.53 (1H, s)

CI-MS (m/e): 208 (M+1)

Example I-18

Preparation of 6,7-bis(2-methoxyethoxy)-quinazolin-4-one

In a 10-mL volume stainless steel pressure-resistant vessel were placed 1.00 g (2.8 mmol) of 4,5-bis(2-methoxyethoxy)anthranilic acid, 0.93 g (8.8 mmol) of methyl orthoformate, 0.67 g (8.8 mmol) of ammonium acetate, and 5.0 mL of methanol. The reaction was carried out at 95° C. for 8 hours. After the reaction was complete, the reaction mixture was cooled to room temperature and concentrated under reduced pressure. Then, the concentrate was recrystallized from 20 mL of methanol. The crystalline product was collected by filtration and dried under reduced pressure to give 0.85 g (isolated yield: 83%) of 6,7-bis(2-methoxyethoxy)quinazolin-4-one as a white crystalline product.

6,7-Bis(2-methoxyethoxy)quinazolin-4-one had the following characteristics.

$^1$H-NMR ($D_2O$, δ (ppm)): 3.49 (3H, s), 3.50 (3H, s), 3.86-3.88 (4H, m), 3.97 (2H, d, J=3.6 Hz), 4.04 (2H, d, J=3.6 Hz), 6.41 (1H, s), 6.72 (1H, s), 7.72 (1H, s)

CI-MS (m/e): 295 (M+1)

Example I-19

Preparation of 6,7-bis(2-methoxyethoxy)-quinazolin-4-one

In a 10-mL volume stainless steel pressure-resistant vessel were placed 1.02 g (3.3 mmol) of ethyl 4,5-bis(2-methoxyethoxy)anthranilate, 0.96 g (9.1 mmol) of methyl orthoformate, 0.69 g (9.1 mmol) of ammonium acetate, and 5.0 mL of methanol. The reaction was carried out at 110° C. for 6 hours. After the reaction was complete, the reaction mixture was cooled to room temperature and concentrated under reduced pressure. Then, the concentrate was recrystallized from 20 mL of methanol. The crystalline product was collected by filtration and dried under reduced pressure to give 0.87 g (isolated yield: 91%) of 6,7-bis(2-methoxyethoxy)quinazolin-4-one as a white crystalline product.

Example I-20

Preparation of 6-methoxy-7-(3-morpholinopropoxy)quinazolin-4-one

In a 100-mL volume stainless steel pressure-resistant vessel were placed 5.80 g (17.9 mmol) of methyl 5-methoxy-4-(3-morpholinopropoxy)anthranilate, 3.79 g (35.8 mmol) of methyl orthoformate, 2.56 g (33.2 mmol) of ammonium acetate, and 30 mL of methanol. The reaction was carried out at 115° C. for 5 hours. After the reaction was complete, the reaction mixture was cooled to room temperature and concentrated under reduced pressure. Then, the concentrate was recrystallized from 100 mL of methanol. The crystalline product was collected by filtration and dried under reduced pressure to give 4.97 g (isolated yield: 87%) of 6-methoxy-7-(3-morpholinopropoxy)-quinazolin-4-one as a white crystalline product.

6-Methoxy-7-(3-morpholinopropoxy)quinazolin-4-one had the following characteristics.

$^1$H-NMR (DMSO-$d_6$, δ (ppm)): 2.08-2.13 (2H, m), 2.48 (4H, t, J=4.5 Hz), 2.56 (2H, t, J=6.9 Hz), 3.73 (4H, t, J=4.5 Hz), 4.00 (3H, s), 4.24 (2H, t, J=6.6 Hz), 7.18 (1H, s), 7.60 (1H, s), 8.02 (1H, s), 10.5 (1H, brs)

CI-MS (m/e): 320 (M+1)

Example I-21

Preparation of 6-methoxy-7-(3-piperidinopropoxy)quinazolin-4-one

In a 10-mL volume stainless steel pressure-resistant vessel were placed 1.00 mg (3.1 mmol) of methyl 5-methoxy-4-(3-piperidinopropoxy)anthranilate, 0.99 g (9.3 mmol) of methyl orthoformate, 0.72 g (9.3 mmol) of ammonium acetate, and 5.0 mL of methanol. The reaction was carried out at 120° C. for 5 hours. After the reaction was complete, the reaction mixture was cooled to room temperature and analyzed (according to absolute quantitative analysis) by high performance liquid chromatography. There was produced 0.89 mg (reaction yield: 90%) of 6-methoxy-7-(3-piperidinopropoxy)quinazolin-4-one.

Example II-1

Preparation of methyl 4-(2-chloroethoxy)-3-methoxybenzoate

In a 50 mL volume glass flask equipped with a stirrer, a thermometer and a reflux condenser were placed 1.00 g (5.49 mmol) of methyl 4-hydroxy-3-methoxybenzoate (purity: 98 wt. %), 1.04 g (7.14 mmol) of 2-bromo-1-chloroethane (purity: 98 wt. %), 0.85 g (6.04 mmol) of potassium carbonate (purity: 98 wt. %), and 30 mL of acetonitrile. The resulting mixture was refluxed under stirring at 80-85° C. for 8 hours in an argon gas atmosphere. After the reaction was complete, the reaction mixture was filtered and concentrated under reduced pressure. To the concentrate was added 20 mL of n-heptane, to precipitate a crystalline product. The crystalline product was collected by filtration and dried under reduced pressure, to obtain 1.34 g (isolated yield: 97.8%, purity: 98% in terms of area percentage determined by high performance liquid chromatography) of methyl 4-(2-chloroethoxy)-3-methoxybenzoate as a white crystalline product.

Methyl 4-(2-chloroethoxy)-3-methoxybenzoate had the following characteristics.

m.p.: 61-62° C.

$^1$H-NMR (CDCl$_3$, δ (ppm)): 3.65-3.69 (2H, m), 3.82 (3H, s), 3.90 (3H, s), 4.35 (2H, t, J=3.0 Hz), 6.95 (1H, d, J=6.0 Hz), 7.57 (1H, s), 7.67 (1H, d, J=6.0 Hz)

Example II-2

Preparation of methyl 4-(2-chloroethoxy)-5-methoxy-2-nitrobenzoate

In a 50 mL volume glass flask equipped with a stirrer, a thermometer and a dropping funnel were placed 1.02 g (4.09 mmol) of methyl 4-(2-chloroethoxy)-3-methoxybenzoate (purity: 98%) obtained in Example II-1, 0.03 g (0.40 mmol) of sodium nitrite, and 1.25 mL of acetic acid. The resulting mixture was heated to 40° C. under stirring. To the reaction mixture was dropwise added slowly 1.72 g (16.5 mmol) of nitric acid (60 wt. %), and the mixture was heated at 40-50° C. for 5 hours. After the reaction was complete, 5 mL of water was added to the reaction mixture, and the aqueous mixture was cooled to 20° C., precipitating a crystalline product. The crystalline product was collected by filtration and dried under reduced pressure, to give 1.12 g (isolated yield: 93.0%, purity: 98% in terms of area percentage determined by high performance liquid chromatography) of methyl 4-(2-chloroethoxy)-5-methoxy-2-nitrobenzoate as a white crystalline product.

Methyl 4-(2-chloroethoxy)-5-methoxy-2-nitrobenzoate had the following characteristics.

m.p.: 116-117° C.

$^1$H-NMR (CDCl$_3$, δ (ppm)): 3.65-3.69 (2H, m), 3.90 (3H, s), 3.91 (3H, s), 4.35 (2H, t, J=6.0 Hz), 7.09 (1H, s), 7.49 (1H, s)

Example II-3

Preparation of methyl 4-(3-chloropropoxy)-3-methoxybenzoate

In a 50 mL volume glass flask equipped with a stirrer, a thermometer, a dropping funnel and a reflux condenser were placed 1.02 g (5.49 mmol) of methyl 4-hydroxy-3-methoxybenzoate (purity: 98 wt. %), 1.15 g (7.14 mmol) of 3-bromo-1-chloropropane (purity: 98 wt. %), 0.85 g (6.04 mmol) of potassium carbonate (purity: 98 wt. %), and 30 mL of acetonitrile. The resulting mixture was refluxed under stirring at 80-85° C. for 8 hours in an argon gas atmosphere. After the reaction was complete, the reaction mixture was filtered and concentrated under reduced pressure. To the concentrate was added n-heptane, to precipitate a crystalline product. The crystalline product was collected by filtration and dried under reduced pressure, to obtain 1.34 g (isolated yield: 97.8%, purity: 98% in terms of area percentage determined by high performance liquid chromatography) of methyl 4-(3-chloropropoxy)-3-methoxybenzoate as a white crystalline product.

Methyl 4-(3-chloropropoxy)-3-methoxybenzoate had the following characteristics.

m.p.: 98-99° C.

$^1$H-NMR (CDCl$_3$, δ (ppm)): 2.27-2.35 (2H, m), 3.75-3.79 (2H, m), 3.85 (3H, s), 3.91 (3H, s), 4.22 (2H, t, J=6.0 Hz), 6.95 (1H, d, J=6.0 Hz), 7.57 (1H, s), 7.67 (1H, d, J=6.0 Hz)

Example II-4

Preparation of methyl 4-(3-chloropropoxy)-5-methoxy-2-nitrobenzoate

In a 100 mL volume glass flask equipped with a stirrer, a thermometer and a dropping funnel were placed 10.1 g (38.7 mmol) of methyl 4-(3-chloropropoxy)-3-methoxybenzoate (purity: 98%) obtained in the manner described in Example II-3, 0.27 g (3.87 mmol) of sodium nitrite, and 12.5 mL of acetic acid. The resulting mixture was heated to 40-50° C. under stirring. To the reaction mixture was dropwise added slowly 16.2 g (154.8 mmol) of nitric acid (60 wt. %), and the mixture was kept at the same temperature for 5 hours. After the reaction was complete, 20 mL of water was added to the reaction mixture, and the aqueous mixture was cooled to 20° C., precipitating a crystalline product. The crystalline product was collected by filtration, washed successively with 30 mL of water and 30 mL of n-heptane, and dried under reduced pressure, to give 10.9 g (isolated yield: 92.0%, purity: 98% in terms of area percentage determined by high performance liquid chromatography) of methyl 4-(3-chloropropoxy)-5-methoxy-2-nitrobenzoate as a white crystalline product.

Methyl 4-(3-chloropropoxy)-5-methoxy-2-nitrobenzoate had the following characteristics.

m.p.: 63-64° C.

$^1$H-NMR (CDCl$_3$, δ (ppm)): 2.29-2.37 (2H, m), 3.67-3.79 (2H, m), 3.87 (3H, s), 3.96 (3H, s), 7.08 (1H, s), 7.50 (1H, s)

Example II-5

Preparation of methyl 4-(3-chloropropoxy)-5-methoxy-2-nitrobenzoate

In a 200 mL volume glass flask equipped with a stirrer, a thermometer, a dropping funnel and a reflux condenser were placed 11.2 g (71.4 mmol) of 3-bromo-1-chloropropane (purity: 98 wt. %), 8.52 g (60.4 mmol) of potassium carbonate (purity: 98 wt. %), and 40 mL of acetone. The resulting mixture was refluxed under stirring at 52-57° C. in an argon gas atmosphere. To the mixture was then added slowly a solution of 10.2 g (54.9 mmol) of methyl 4-hydroxy-3-methoxybenzoate in 40 mL of acetone for 30 minutes, and the mixture was heated at the same temperature for 5 hours. After the reaction was complete, the reaction mixture was filtered and concentrated under reduced pressure, to give 17.0 g of a solution mainly containing methyl 4-(3-chloropropoxy)-3-methoxybenzoate.

In a 100 mL volume glass flask equipped with a stirrer, a thermometer and a dropping funnel were placed 14.0 of the above-obtained solution mainly containing methyl 4-(3-chloropropoxy)-3-methoxybenzoate, 0.20 g (2.60 mmol) of sodium nitrite, and 17.5 mL of acetic acid. The resulting mixture was heated to 40-50° C. under stirring. To the reaction mixture was dropwise added slowly 22.4 g (215.2 mmol) of nitric acid (60 wt. %), and the mixture was kept at the same temperature for 2 hours. After the reaction was complete, 42 mL of water was added to the reaction mixture. Then, the organic portion was separated and washed with warm water. Analysis of the organic portion by high performance liquid chromatography (absolute quantitative analysis) indicated that 15.7 g (reaction yield: 96.2%) of methyl 4-(3-chloropropoxy)-5-methoxy-2-nitrobenzoate was produced.

Example II-6

Preparation of methyl 4-(3-chloropropoxy)-5-methoxy-2-nitrobenzoate

In a one liter volume glass flask equipped with a stirrer, a thermometer, a dropping funnel and a reflux condenser were placed 105.9 g (659 mmol) of 3-bromo-1-chloropropane (purity: 98 wt. %), 58.1 g (411 mmol) of potassium carbonate (purity: 98 wt. %), and 300 mL of acetone. The resulting mixture was refluxed under stirring at 52-57° C. in an argon gas atmosphere. To the mixture was then added slowly a solution of 51.0 g (247 mmol) of methyl 4-hydroxy-3-methoxybenzoate in 200 mL of acetone for 30 minutes, and the mixture was heated at the same temperature for 2 hours. After the reaction was complete, the reaction mixture was filtered and concentrated under reduced pressure, to give 138.0 g of a solution mainly containing methyl 4-(3-chloropropoxy)-3-methoxybenzoate.

In a 500 mL volume glass flask equipped with a stirrer, a thermometer and a dropping funnel were placed 138.0 of the solution mainly containing methyl 4-(3-chloropropoxy)-3-methoxybenzoate, 0.93 g (13.7 mmol) of sodium nitrite, and 90 mL of acetic acid. The resulting mixture was heated to 40-50° C. under stirring. To the reaction mixture was dropwise added slowly 111.5 g (215.2 mmol) of nitric acid (60 wt. %), and the mixture was kept at the same temperature for 2 hours. After the reaction was complete, 210 mL of water was added to the reaction mixture. Then, the organic portion was separated and washed with 210 mL of warm water. Analysis of the organic portion by high performance liquid chromatography (absolute quantitative analysis) indicated that 78.7 g (reaction yield: 94.5%) of methyl 4-(3-chloropropoxy)-5-methoxy-2-nitrobenzoate was produced.

Example II-7

Preparation of methyl 4-(3-chloropropoxy)-3-methoxybenzoate

In a 50 mL volume glass flask equipped with a stirrer, a thermometer, a dropping funnel and a reflux condenser were placed 1.02 g (5.49 mmol) of methyl 4-hydroxy-3-methoxybenzoate (purity: 98 wt. %), 2.12 g (13.2 mmol) of 3-bromo-1-chloropropane (purity: 98 wt. %), 1.16 g (8.24 mmol) of potassium carbonate (purity: 98 wt. %), and 10 mL of acetonitrile. The resulting mixture was refluxed under stirring at 80-85° C. in an argon gas atmosphere for 5 hours. After the reaction was complete, the reaction mixture was filtered. Analysis of the filtrate by high performance liquid chromatography (absolute quantitative analysis) indicated that 1.38 g (reaction yield: 97.0%) of methyl 4-(3-chloropropoxy)-3-methoxybenzoate was produced.

Example II-8

Preparation of methyl 4-(3-chloropropoxy)-3-methoxybenzoate

In a 50 mL volume glass flask equipped with a stirrer, a thermometer, a dropping funnel and a reflux condenser were placed 1.02 g (5.49 mmol) of methyl 4-hydroxy-3-methoxybenzoate (purity: 98 wt. %), 3.17 g (19.8 mmol) of 3-bromo- 1-chloropropane (purity: 98 wt. %), 1.16 g (8.24 mmol) of potassium carbonate (purity: 98 wt. %), and 10 mL of acetonitrile. The resulting mixture was refluxed under stirring at 80-85° C. in an argon gas atmosphere for 5 hours. After the reaction was complete, the reaction mixture was filtered. Analysis of the filtrate by high performance liquid chromatography (absolute quantitative analysis) indicated that 1.41 g (reaction yield: 98.9%) of methyl 4-(3-chloropropoxy)-3-methoxybenzoate was produced.

Example II-9

Preparation of methyl 4-(3-chloropropoxy)-3-methoxybenzoate

In a 50 mL volume glass flask equipped with a stirrer, a thermometer, a dropping funnel and a reflux condenser were placed 1.02 g (5.49 mmol) of methyl 4-hydroxy-3-methoxybenzoate (purity: 98 wt. %), 2.12 g (13.2 mmol) of 3-bromo-1-chloropropane (purity: 98 wt. %), 1.16 g (8.24 mmol) of potassium carbonate (purity: 98 wt. %), and 10 mL of methyl ethyl ketone. The resulting mixture was refluxed under stirring at 77-82° C. in an argon gas atmosphere for 2 hours. After the reaction was complete, the reaction mixture was filtered. Analysis of the filtrate by high performance liquid chromatography (absolute quantitative analysis) indicated that 1.36 g (reaction yield: 95.4%) of methyl 4-(3-chloropropoxy)-3-methoxybenzoate was produced.

Example II-10

Preparation of methyl 4-(3-chloropropoxy)-3-methoxybenzoate

In a 50 mL volume glass flask equipped with a stirrer, a thermometer, a dropping funnel and a reflux condenser were placed 1.02 g (5.49 mmol) of methyl 4-hydroxy-3-methoxybenzoate (purity: 98 wt. %), 2.12 g (13.2 mmol) of 3-bromo-1-chloropropane (purity: 98 wt. %), 1.16 g (8.24 mmol) of potassium carbonate (purity: 98 wt. %), and 30 mL of methanol. The resulting mixture was under stirring at 62-67° C. in an argon gas atmosphere for 10 hours. After the reaction was complete, the reaction mixture was filtered. Analysis of the filtrate by high performance liquid chromatography (absolute quantitative analysis) indicated that 1.23 g (reaction yield: 86.5%) of methyl 4-(3-chloropropoxy)-3-methoxybenzoate was produced.

Example II-11

Preparation of methyl 4-(3-chloropropoxy)-3-methoxybenzoate

In a 50 mL volume glass flask equipped with a stirrer, a thermometer, a dropping funnel and a reflux condenser were placed 1.02 g (5.49 mmol) of methyl 4-hydroxy-3-methoxybenzoate (purity: 98 wt. %), 2.12 g (13.2 mmol) of 3-bromo-1-chloropropane (purity: 98 wt. %), 1.16 g (8.24 mmol) of potassium carbonate (purity: 98 wt. %), and 10 mL of N,N-dimethylformamide. The resulting mixture was refluxed under stirring at 52-57° C. in an argon gas atmosphere for 5 hours. After the reaction was complete, the reaction mixture was filtered. Analysis of the filtrate by high performance liquid chromatography (absolute quantitative analysis) indicated that 0.85 g (reaction yield: 59.8%) of methyl 4-(3-chloropropoxy)-3-methoxybenzoate was produced.

Example II-12

Preparation of methyl 4-(3-chloropropoxy)-3-methoxybenzoate

In a 50 mL volume glass flask equipped with a stirrer, a thermometer, a dropping funnel and a reflux condenser were placed 1.02 g (5.49 mmol) of methyl 4-hydroxy-3-methoxybenzoate (purity: 98 wt. %), 2.12 g (13.2 mmol) of 3-bromo-1-chloropropane (purity: 98 wt. %), 1.16 g (8.24 mmol) of potassium carbonate (purity: 98 wt. %), and 10 mL of acetone. The resulting mixture was refluxed under stirring at 55-60° C. in an argon gas atmosphere for 5 hours. After the reaction was complete, the reaction mixture was filtered. Analysis of the filtrate by high performance liquid chromatography (absolute quantitative analysis) indicated that 1.38 g (reaction yield: 97.2%) of methyl 4-(3-chloropropoxy)-3-methoxybenzoate was produced.

Example II-13

Preparation of methyl 4-(3-chloropropoxy)-3-methoxybenzoate

In a 50 mL volume glass flask equipped with a stirrer, a thermometer, a dropping funnel and a reflux condenser were placed 1.02 g (5.49 mmol) of methyl 4-hydroxy-3-methoxybenzoate (purity: 98 wt. %), 2.12 g (13.2 mmol) of 3-bromo-1-chloropropane (purity: 98 wt. %), 1.16 g (8.24 mmol) of potassium carbonate (purity: 98 wt. %), 5 mL of acetone, and 5 mL of acetonitrile. The resulting mixture was refluxed under stirring at 79-75° C. in an argon gas atmosphere for 5 hours. After the reaction was complete, the reaction mixture was filtered. Analysis of the filtrate by high performance liquid chromatography (absolute quantitative analysis) indicated that 1.41 g (reaction yield: 99.3%) of methyl 4-(3-chloropropoxy)-3-methoxybenzoate was produced.

Example II-14

Preparation of methyl 4-(3-chloropropoxy)-3-methoxybenzoate

In a 50 mL volume glass flask equipped with a stirrer, a thermometer, a dropping funnel and a reflux condenser were placed 1.02 g (5.49 mmol) of methyl 4-hydroxy-3-methoxybenzoate (purity: 98 wt. %), 2.12 g (13.2 mmol) of 3-bromo-1-chloropropane (purity: 98 wt. %), 1.16 g (8.24 mmol) of potassium carbonate (purity: 98 wt. %), 1.02 g (13.7 mmol) of potassium chloride, and 10 mL of acetone. The resulting mixture was refluxed under stirring at 55-60° C. in an argon gas atmosphere for 10 hours. After the reaction was complete, the reaction mixture was filtered. Analysis of the filtrate by high performance liquid chromatography (absolute quantitative analysis) indicated that 1.39 g (reaction yield: 98.2%) of methyl 4-(3-chloropropoxy)-3-methoxybenzoate was produced.

Example II-15

Preparation of methyl 4-(3-chloropropoxy)-3-methoxybenzoate

In a 50 mL volume glass flask equipped with a stirrer, a thermometer, a dropping funnel and a reflux condenser were placed 1.02 g (5.49 mmol) of methyl 4-hydroxy-3-methoxybenzoate (purity: 98 wt. %), 2.12 g (13.2 mmol) of 3-bromo- 1-chloropropane (purity: 98 wt. %), 1.16 g (8.24 mmol) of potassium carbonate (purity: 98 wt. %), 1.02 g (17.5 mmol) of sodium chloride, and 10 mL of acetone. The resulting mixture was refluxed under stirring at 55-60° C. in an argon gas atmosphere for 5 hours. After the reaction was complete, the reaction mixture was filtered. Analysis of the filtrate by high performance liquid chromatography (absolute quantitative analysis) indicated that 1.41 g (reaction yield: 99.5%) of methyl 4-(3-chloropropoxy)-3-methoxybenzoate was produced.

Example II-16

Preparation of methyl
4-(3-bromopropoxy)-3-methoxybenzoate

In a 100 mL volume glass flask equipped with a stirrer, a thermometer, a dropping funnel and a reflux condenser were placed 10.2 g (54.9 mmol) of methyl 4-hydroxy-3-methoxybenzoate (purity: 98 wt. %), 12.5 g (60.4 mmol) of 1,3-dibromopropane (purity: 99 wt. %), 8.5 g (60.4 mmol) of potassium carbonate (purity: 98 wt. %), and 30 mL of acetonitrile. The resulting mixture was refluxed under stirring at 80-85° C. in an argon gas atmosphere for 8 hours. After the reaction was complete, the reaction mixture was filtered and concentrated under reduced pressure. The concentrate was purified by silica gel column chromatography (gel: Wako gel C-200, eluent: n-hexane), to give 15.1 g (isolated yield: 88.8%, purity: 98% in terms of area percentage by high performance liquid chromatography) of methyl 4-(3-bromopropoxy)-3-methoxybenzoate as a white crystalline product.

Methyl 4-(3-bromopropoxy)-3-methoxybenzoate had the following characteristics.

m.p.: 65-66° C.
$^1$H-NMR (CDCl$_3$, δ (ppm)): 2.01-2.43 (2H, m), 3.61-3.65 (2H, m), 3.89 (3H, s), 3.93 (3H, s), 4.19 (2H, t, J=6.0 Hz), 6.90 (1H, d, J=6.0 Hz), 7.55 (1H, s), 7.67 (1H, d, J=6.0 Hz)

Example II-17

Preparation of methyl
5-methoxy-4-(3-bromopropoxy)-2-nitrobenzoate

In a 100 mL volume glass flask equipped with a stirrer, a thermometer and a dropping funnel were placed 10.2 g (33.0 mmol) of methyl 4-(3-bromopropoxy)-3-methoxybenzoate (purity: 98%) obtained in Example II-16, 0.23 g (3.30 mmol) of sodium nitrite, and 12.5 mL of acetic acid. The resulting mixture was heated to 40° C. under stirring. To the reaction mixture was dropwise added slowly 13.8 g (132.0 mmol) of nitric acid (60 wt. %), and the mixture was heated at 40-50° C. for 5 hours. After the reaction was complete, 30 mL of water was added to the reaction mixture, and the aqueous mixture was cooled to 20° C., precipitating a crystalline product. The crystalline product was collected by filtration, washed successively with 30 mL of water and 30 mL of n-heptane, and dried under reduced pressure, to give 10.7 g (isolated yield: 92.0%, purity: 99% in terms of area percentage determined by high performance liquid chromatography) of methyl 5-methoxy-4-(3-bromopropoxy)-2-nitrobenzoate as a white crystalline product.

Methyl 5-methoxy-4-(3-bromopropoxy)-2-nitrobenzoate had the following characteristics.

m.p.: 71-72° C.
$^1$H-NMR (CDCl$_3$, δ (ppm)): 2.37-2.45 (2H, m), 3.60-3.66 (2H, m), 3.90 (3H, s), 3.96 (3H, s), 7.08 (1H, s), 7.50 (1H, s)

Example II-18

Preparation of methyl
4-(4-chlorobutoxy)-3-methoxybenzoate

In a 100 mL volume glass flask equipped with a stirrer, a thermometer and a reflux condenser were placed 10.2 g (54.9 mmol) of methyl 4-hydroxy-3-methoxybenzoate (purity: 98 wt. %), 12.6 g (71.4 mmol) of 4-bromo-1-chlorobutane (purity: 99 wt. %), 8.5 g (60.4 mmol) of potassium carbonate (purity: 98 wt. %), and 300 mL of acetonitrile. The resulting mixture was refluxed under stirring at 80-85° C. for 8 hours in an argon gas atmosphere. After the reaction was complete, the reaction mixture was filtered and concentrated under reduced pressure. The concentrate was purified by silica gel column chromatography (gel: Wako gel C-200, eluent: n-hexane), to give 13.6 g (isolated yield: 90.0%, purity: 99% in terms of area percentage by high performance liquid chromatography) of methyl 4-(4-chlorobutoxy)-3-methoxybenzoate as a colorless liquid.

Methyl 4-(4-chlorobutoxy)-3-methoxybenzoate was a new compound and had the following characteristics.

$^1$H-NMR (CDCl$_3$, δ (ppm)): 1.96-2.07 (4H, m), 3.61-3.67 (2H, m), 3.89 (3H, s), 3.93 (3H, s), 4.13 (2H, t, J=6.0 Hz), 6.87 (1H, d, J=6.0 Hz), 7.55 (1H, s), 7.64 (1H, d, J=7 Hz)

Example II-19

Preparation of methyl
5-methoxy-4-(4-chlorobutoxy)-2-nitrobenzoate

In a 50 mL volume glass flask equipped with a stirrer, a thermometer and a dropping funnel were placed 10.1 g (36.7 mmol) of methyl 4-(4-chlorobutoxy)-3-methoxybenzoate (purity: 98%) obtained in Example II-18, 0.25 g (3.67 mmol) of sodium nitrite, and 12.5 mL of acetic acid. The resulting mixture was heated to 40° C. under stirring. To the reaction mixture was dropwise added slowly 115.4 g (146.8 mmol) of nitric acid (60 wt. %), and the mixture was heated at 40-50° C. for 5 hours. After the reaction was complete, 20 mL of water was added to the reaction mixture, and the aqueous mixture was cooled to 20° C., precipitating a crystalline product. The crystalline product was collected by filtration, washed successively with 30 mL of water and 30 mL of n-heptane, and dried under reduced pressure, to give 10.9 g (isolated yield: 92.0%, purity: 99% in terms of area percentage determined by high performance liquid chromatography) of methyl 5-methoxy-4-(4-chlorobutoxy)-2-nitrobenzoate as a white crystalline product.

Methyl 5-methoxy-4-(4-chlorobutoxy)-2-nitrobenzoate was a new compound and had the following characteristics.

m.p.: 74-75° C.
$^1$H-NMR (CDCl$_3$, δ (ppm)): 1.95-2.10 (4H, m), 3.61-3.66 (2H, m), 3.89 (3H, s), 3.93 (3H, s), 4.13 (2H, t, J=6.0 Hz), 6.87 (1H, d, J=6.0 Hz), 7.26 (1H, s), 7.44 (1H, s)

Example II-20

Preparation of methyl
3-(3-chloropropoxy)-4-methoxybenzoate

In a 100 mL volume glass flask equipped with a stirrer, a thermometer and a reflux condenser were placed 10.2 g (54.9 mmol) of methyl 3-hydroxy-4-methoxybenzoate (purity: 98 wt. %), 11.5 g (71.4 mmol) of 3-bromo-1-chloropropane (purity: 98 wt. %), 8.5 g (60.4 mmol) of potassium carbonate (purity: 98 wt. %), and 30 mL of acetone. The resulting mixture was refluxed under stirring at 80-85° C. for 8 hours in an argon gas atmosphere. After the reaction was complete, the reaction mixture was filtered. To the concentrate was added n-heptane, to precipitate a crystalline product. The crystalline product was collected and dried under reduced pressure, to give 13.7 g (isolated yield: 95.8%, purity: 99% in terms of area percentage by high performance liquid chromatography) of methyl 3-(3-chloropropoxy)-4-methoxybenzoate as a white crystalline product.

Methyl 3-(3-chloropropoxy)-4-methoxybenzoate had the following characteristics.

m.p.: 46-48° C.

$^1$H-NMR (CDCl$_3$, δ (ppm)): 2.27-2.33 (2H, m), 3.64-3.75 (2H, m), 3.79 (3H, s), 3.91 (3H, s), 4.21 (2H, t, J=5.0 Hz), 6.88 (1H, d, J=6.0 Hz), 7.67 (1H, d, J=6.0 Hz), 7.58 (1H, s), 7.70 (1H, d, J=6.0 Hz)

Example II-21

Preparation of methyl 4-methoxy-5-(3-chloropropoxy)-2-nitrobenzoate

In a 50 mL volume glass flask equipped with a stirrer, a thermometer and a dropping funnel were placed 10.1 g (38.7 mmol) of methyl 3-(3-chloropropoxy)-4-methoxybenzoate (purity: 99%) obtained in Example II-20, 0.27 g (3.87 mmol) of sodium nitrite, and 12.5 mL of acetic acid. The resulting mixture was heated to 40° C. under stirring. To the reaction mixture was dropwise added slowly 16.2 g (154.8 mmol) of nitric acid (60 wt. %), and the mixture was heated at 40-50° C. for 5 hours. After the reaction was complete, 20 mL of water was added to the reaction mixture, and the aqueous mixture was cooled to 20° C., precipitating a crystalline product. The crystalline product was collected by filtration, washed successively with 30 mL of water and 30 mL of n-heptane, and dried under reduced pressure, to give 11.3 g (isolated yield: 95.0%, purity: 99% in terms of area percentage determined by high performance liquid chromatography) of methyl 4-methoxy-5-(3-chloropropoxy)-2-nitrobenzoate as a white crystalline product.

4-Methoxy-5-(3-chloropropoxy)-2-nitrobenzoate had the following characteristics.

m.p.: 63-64° C.

$^1$H-NMR (CDCl$_3$, δ (ppm)): 2.28-2.37 (2H, m), 3.64-3.75 (2H, m), 3.89 (3H, s), 3.99 (3H, s), 4.24 (2H, t, J=5.0 Hz), 7.11 (1H, s), 7.45 (1H, s)

Reference Example III-1

Preparation of methyl 4-(2-chloroethoxy)-3-methoxybenzoate

In a 50 mL volume glass flask equipped with a stirrer, a thermometer and a reflux condenser were placed 1.00 g (5.49 mmol) of methyl 4-hydroxy-3-methoxybenzoate (purity: 98 wt. %), 1.02 g (7.14 mmol) of 2-bromo-1-chloroethane, 0.83 g (6.04 mmol) of potassium carbonate, and 30 mL of acetonitrile. The resulting mixture was refluxed under stirring at 80-85° C. for 8 hours in an argon gas atmosphere. After the reaction was complete, the reaction mixture was filtered and concentrated under reduced pressure. To the concentrate was added 20 mL of n-heptane, to precipitate a crystalline product. The crystalline product was collected by filtration and dried under reduced pressure, to obtain 1.34 g (isolated yield: 97.8%) of methyl 4-(2-chloroethoxy)-3-methoxybenzoate as a white crystalline product.

Methyl 4-(2-chloroethoxy)-3-methoxybenzoate had the following characteristics.

m.p.: 61-62° C.

$^1$H-NMR (CDCl$_3$, δ (ppm)): 3.65-3.69 (2H, m), 3.82 (3H, s), 3.90 (3H, s), 4.35 (2H, t, J=3.0 Hz), 6.95 (1H, d, J=6.0 Hz), 7.57 (1H, s), 7.67 (1H, d, J=6.0 Hz)

Reference Example III-2

Preparation of methyl 5-methoxy-4-(2-chloroethoxy)-2-nitrobenzoate

In a 50 mL volume glass flask equipped with a stirrer, a thermometer and a dropping funnel were placed 1.02 g (4.08 mmol) of methyl 4-(2-chloroethoxy)-3-methoxybenzoate (purity: 98%) obtained in Reference Example III-1, 0.03 g (0.40 mmol) of sodium nitrite, and 1.25 mL of acetic acid. The resulting mixture was heated to 40° C. under stirring. To the reaction mixture was dropwise added slowly 1.72 g (16.5 mmol) of nitric acid (60 wt. %), and the mixture was heated to the same temperature for 5 hours. After the reaction was complete, 5 mL of water was added to the reaction mixture, and the aqueous mixture was cooled to 20° C., precipitating a crystalline product. The crystalline product was collected by filtration, washed with 5 mL of water, and dried under reduced pressure, to give 1.12 g (isolated yield: 93.0%, purity: 98% in terms of area percentage determined by high performance liquid chromatography) of methyl 5-methoxy-4-(2-chloroethoxy)-2-nitrobenzoate as a white crystalline product.

5-Methoxy-4-(2-chloroethoxy)-2-nitrobenzoate had the following characteristics.

m.p.: 116-117° C.

$^1$H-NMR (CDCl$_3$, δ (ppm)): 3.65-3.69 (2H, m), 3.90 (3H, s), 3.91 (3H, s), 4.35 (2H, t, J=6.0 Hz), 7.09 (1H, s), 7.49 (1H, s)

Example III-1

Preparation of methyl 5-methoxy-4-(2-chloroethoxy)anthranilate

In a 50 mL volume glass flask equipped with a stirrer, a thermometer, a reflux condenser and a gas inlet were placed 1.02 g (3.45 mmol) of methyl 5-methoxy-4-(2-chloroethoxy)-2-nitrobenzoate (purity: 98%) obtained in Reference Example III-2 and 20 mL of methanol. The resulting mixture was heated to 50° C. under stirring. To the mixture was added 0.5 g of 3 wt. % platinum sulfide/carbon (containing 65.7% water) at the same temperature. The resulting mixture was heated to the same temperature for one hour, while hydrogen was introduced to the mixture under atmospheric pressure at a rate of 50 mL/min. After the reaction was complete, the reaction mixture was filtered and the filtrate was concentrated under reduced pressure, to precipitate a crystalline product. The crystalline product was dried under reduced pressure, to give 0.91 g (isolated yield: 93.0%, purity: 99% in terms of area percentage determined by high performance liquid chromatography) of methyl 5-methoxy-4-(2-chloroethoxy)-anthranilate as a white crystalline product.

Methyl 5-methoxy-4-(2-chloroethoxy)anthranilate had the following characteristics.

m.p.: 112-113° C.

$^1$H-NMR (CDCl$_3$, δ (ppm)): 3.77 (3H, s), 3.79 (3H, s) 3.81-3.92 (2H, m), 4.25 (2H, t, J=6.0 Hz), 5.56 (2H, brs), 6.15 (1H, s), 7.34 (1H, s)

Reference Example III-3

Preparation of methyl
4-(3-chloropropoxy)-3-methoxybenzoate

In a 100 mL volume glass flask equipped with a stirrer, a thermometer, a dropping funnel and a reflux condenser were placed 10.2 g (54.9 mmol) of methyl 4-hydroxy-3-methoxybenzoate (purity: 98 wt. %), 11.2 g (71.4 mmol) of 3-bromo-1-chloropropane, 8.3 g (60.4 mmol) of potassium carbonate, and 30 mL of acetonitrile. The resulting mixture was refluxed under stirring at 80-85° C. for 8 hours in an argon gas atmosphere. After the reaction was complete, the reaction mixture was filtered and concentrated under reduced pressure. To the concentrate was added n-heptane, to precipitate a crystalline product. The crystalline product was collected by filtration and dried under reduced pressure, to obtain 14.3 g (isolated yield: 97.8%, purity: 98% in terms of area percentage determined by high performance liquid chromatography) of methyl 4-(3-chloropropoxy)-3-methoxybenzoate as a white crystalline product.

Methyl 4-(3-chloropropoxy)-3-methoxybenzoate had the following characteristics.

m.p.: 98-99° C.

$^1$H-NMR (CDCl$_3$, δ (ppm)): 2.27-2.35 (2H, m), 3.75-3.79 (2H, m), 3.85 (3H, s), 3.91 (3H, s), 4.22 (2H, t, J=6.0 Hz), 6.95 (1H, d, J=6.0 Hz), 7.57 (1H, s), 7.67 (1H, d, J=6.0 Hz)

Reference Example III-4

Preparation of methyl
5-methoxy-4-(3-chloropropoxy)-2-nitrobenzoate

In a 100 mL volume glass flask equipped with a stirrer, a thermometer and a dropping funnel were placed 10.1 g (38.7 mmol) of methyl 4-(3-chloropropoxy)-3-methoxybenzoate (purity: 99%) obtained in Reference Example III-3, 0.27 g (3.87 mmol) of sodium nitrite, and 12.5 mL of acetic acid. The resulting mixture was heated to 40° C. under stirring. To the reaction mixture was dropwise added slowly 16.2 g (154.8 mmol) of nitric acid (60 wt. %), and the mixture was kept at the same temperature for 5 hours. After the reaction was complete, 20 mL of water was added to the reaction mixture, and the aqueous mixture was cooled to 20° C., precipitating a crystalline product. The crystalline product was collected by filtration, washed successively with 30 mL of water and 30 mL of n-heptane, and dried under reduced pressure, to give 10.9 g (isolated yield: 92.0%, purity: 98% in terms of area percentage determined by high performance liquid chromatography) of methyl 5-methoxy-4-(3-chloropropoxy)-2-nitrobenzoate as a white crystalline product.

Methyl 5-methoxy-4-(3-chloropropoxy)-2-nitrobenzoate had the following characteristics.

m.p.: 63-64° C.

$^1$H-NMR (CDCl$_3$, δ (ppm)): 2.29-2.37 (2H, m), 3.67-3.79 (2H, m), 3.87 (3H, s), 3.96 (3H, s), 7.08 (1H, s), 7.50 (1H, s)

Example III-2

Preparation of methyl
5-methoxy-4-(3-chloropropoxy)anthranilate

In a 50 mL volume glass flask equipped with a stirrer, a thermometer, a reflux condenser and a gas inlet were placed 2.02 g (6.58 mmol) of methyl 5-methoxy-4-(3-chloropropoxy)-2-nitrobenzoate (purity: 99%) obtained in Reference Example III-4 and 40 mL of methanol. The resulting mixture was heated to 40° C. under stirring. To the mixture was added 0.2 g of 5 wt. % palladium/carbon (containing 49% water) at the same temperature. The resulting mixture was heated to the same temperature for 2 hours, while hydrogen was introduced to the mixture under atmospheric pressure at a rate of 50 mL/min. After the reaction was complete, the reaction mixture was filtered and the filtrate was concentrated under reduced pressure, to precipitate a crystalline product. The crystalline product was dried under reduced pressure, to give 1.71 g (isolated yield: 98.1%, purity: 98% in terms of area percentage determined by high performance liquid chromatography) of methyl 5-methoxy-4-(3-chloropropoxy)anthranilate as a white crystalline product.

Methyl 5-methoxy-4-(3-chloropropoxy)anthranilate had the following characteristics.

m.p.: 98-99° C.

$^1$H-NMR (CDCl$_3$, δ (ppm)): 2.26-2.33 (2H, m), 2.73-2.76 (2H, m), 3.80 (3H, s), 3.84 (3H, s), 4.13 (2H, t, J=6.0 Hz), 5.46 (2H, brs), 6.18 (1H, s), 7.31 (1H, s)

Example III-3

Preparation of methyl
5-methoxy-4-(3-chloropropoxy)anthranilate

In a 50 mL volume pressure-resistant vessel were placed 2.02 g (6.58 mmol) of methyl 5-methoxy-4-(3-chloropropoxy)-2-nitrobenzoate (purity: 99%) obtained in Reference Example III-4, 2.0 g of a developed Raney nickel, and 40 mL of methanol. The atmosphere in the vessel was replaced with hydrogen, and the vessel was closed. The reaction was carried out at 90-100° C. for 24 hours at a hydrogen pressure of 0.9 MPa (gauge pressure). After the reaction was complete, the reaction mixture was filtered. The filtrate was analyzed by high performance liquid chromatography (absolute quantitative analysis). There was produced 1.71 g (reaction yield: 95.0%) of methyl 5-methoxy-4-(3-chloropropoxy)anthranilate.

Example III-4

Preparation of methyl
5-methoxy-4-(3-chloropropoxy)anthranilate

In a 50 mL volume glass flask equipped with a stirrer, a thermometer, a reflux condenser and a balloon containing hydrogen gas were placed 1.01 g (3.29 mmol) of methyl 5-methoxy-4-(3-chloropropoxy)-2-nitrobenzoate (purity: 99%) obtained in Reference Example III-4, 0.2 g of 3 wt. % platinum sulfide/carbon (containing 65.7% water), and 40 mL of methanol. The reaction was carried out at 40° C. for 8 hours. After the reaction was complete, the reaction mixture was filtered. The filtrate was analyzed by high performance liquid chromatography (absolute quantitative analysis). There was produced 0.88 g (reaction yield: 98.0%) of methyl 5-methoxy-4-(3-chloropropoxy)anthranilate.

Example III-5

Preparation of methyl
5-methoxy-4-(3-chloropropoxy)anthranilate

In a 50 mL volume glass flask equipped with a stirrer, a thermometer and a reflux condenser were placed 1.01 g (3.29 mmol) of methyl 5-methoxy-4-(3-chloropropoxy)-2-nitrobenzoate (purity: 99%) obtained in Reference Example III-4, 0.5 g of 10 wt. % palladium/carbon, and 10 mL of formic acid. The reaction was carried out at 60° C. for 8 hours. After the reaction was complete, the reaction mixture was filtered. The filtrate was analyzed by high performance liquid chromatography (absolute quantitative analysis). There was produced 0.78 g (reaction yield: 87.0%) of methyl 5-methoxy-4-(3-chloropropoxy)-anthranilate.

Example III-6

Preparation of methyl 5-methoxy-4-(3-chloropropoxy)anthranilate

In a 50 mL volume glass flask equipped with a stirrer, a thermometer and a reflux condenser were placed 1.01 g (3.29 mmol) of methyl 5-methoxy-4-(3-chloropropoxy)-2-nitrobenzoate (purity: 99%) obtained in Reference Example III-4, 1.0 g of a developed Raney nickel, and 10 mL of formic acid. The reaction was carried out at 70° C. for 8 hours. After the reaction was complete, the reaction mixture was filtered. The filtrate was analyzed by high performance liquid chromatography (absolute quantitative analysis). There was produced 0.77 g (reaction yield: 85.0%) of methyl 5-methoxy-4-(3-chloropropoxy)-anthranilate.

Example III-7

Preparation of methyl 5-methoxy-4-(3-chloropropoxy)anthranilate

In a 50 mL volume glass flask equipped with a stirrer, a thermometer, a reflux condenser and a gas inlet were placed 1.01 g (3.29 mmol) of methyl 5-methoxy-4-(3-chloropropoxy)-2-nitrobenzoate (purity: 99%) obtained in Reference Example III-4, 0.46 g of 10 wt. % palladium/carbon and 16 mL of methanol. The resulting mixture was heated to 30° C. for 2 hours, while hydrogen was introduced to the mixture under atmospheric pressure at a rate of 50 mL/min. After the reaction was complete, the reaction mixture was filtered. The filtrate was analyzed by high performance liquid chromatography (absolute quantitative analysis). There was produced 0.85 g (reaction yield: 95.2%) of methyl 5-methoxy-4-(3-chloropropoxy)anthranilate.

Reference Example III-5

Preparation of methyl 4-(3-bromopropoxy)-3-methoxybenzoate

In a 100 mL volume glass flask equipped with a stirrer, a thermometer, a dropping funnel and a reflux condenser were placed 10.2 g (54.9 mmol) of methyl 4-hydroxy-3-methoxybenzoate (purity: 98 wt. %), 12.4 g (60.4 mmol) of 1,3-dibromopropane, 8.3 g (60.4 mmol) of potassium carbonate (purity: 98 wt. %), and 30 mL of acetonitrile. The resulting mixture was refluxed under stirring at 80-85° C. in an argon gas atmosphere for 8 hours. After the reaction was complete, the reaction mixture was filtered and concentrated under reduced pressure. The concentrate was purified by silica gel column chromatography (gel: Wako gel C-200, eluent: n-hexane), to give 15.1 g (isolated yield: 88.8%, purity: 98% in terms of area percentage by high performance liquid chromatography) of methyl 4-(3-bromopropoxy)-3-methoxybenzoate as a white crystalline product.

Methyl 4-(3-bromopropoxy)-3-methoxybenzoate had the following characteristics.
m.p.: 65-66° C.
$^1$H-NMR (CDCl$_3$, δ (ppm)): 2.01-2.43 (2H, m), 3.61-3.65 (2H, m), 3.89 (3H, s), 3.93 (3H, s), 4.19 (2H, t, J=6.0 Hz), 6.90 (1H, d, J=6.0 Hz), 7.55 (1H, s), 7.67 (1H, d, J=6.0 Hz)

Reference Example III-6

Preparation of methyl 5-methoxy-4-(3-bromopropoxy)-2-nitrobenzoate

In a 100 mL volume glass flask equipped with a stirrer, a thermometer and a dropping funnel were placed 10.2 g (33.0 mmol) of methyl 4-(3-bromopropoxy)-3-methoxybenzoate (purity: 980%) obtained in Reference Example III-5, 0.23 g (3.30 mmol) of sodium nitrite, and 12.5 mL of acetic acid. The resulting mixture was heated to 40° C. under stirring. To the reaction mixture was dropwise added slowly 13.8 g (132.0 mmol) of nitric acid (60 wt. %), and the mixture was heated at the same temperature for 5 hours. After the reaction was complete, 20 mL of water was added to the reaction mixture, and the aqueous mixture was cooled to 20° C., precipitating a crystalline product. The crystalline product was collected by filtration, washed successively with 30 mL of water and 30 mL of n-heptane, and dried under reduced pressure, to give 10.7 g (isolated yield: 92.0%, purity: 99% in terms of area percentage determined by high performance liquid chromatography) of methyl 5-methoxy-4-(3-bromopropoxy)-2-nitrobenzoate as a white crystalline product.

Methyl 5-methoxy-4-(3-bromopropoxy)-2-nitrobenzoate had the following characteristics.
m.p.: 71-72° C.
$^1$H-NMR (CDCl$_3$, δ (ppm)): 2.37-2.45 (2H, m), 3.60-3.66 (2H, m), 3.90 (3H, s), 3.96 (3H, s), 7.08 (1H, s), 7.50 (1H, s)

Example III-8

Preparation of methyl 5-methoxy-4-(3-bromopropoxy)anthranilate

In a 50 mL volume glass flask equipped with a stirrer, a thermometer, a reflux condenser and a gas inlet were placed 2.02 g (5.75 mmol) of methyl 5-methoxy-4-(3-bromopropoxy)-2-nitrobenzoate (purity: 99%) obtained in Reference Example III-6 and 40 mL of methanol. The resulting mixture was heated to 40° C. under stirring. To the mixture was added 0.2 g of 5 wt. % palladium/carbon (containing 49% water). The resulting mixture was heated to the same temperature for 2 hours, while hydrogen was introduced to the mixture under atmospheric pressure at a rate of 50 mL/min. After the reaction was complete, the reaction mixture was filtered. The filtrate was concentrated under reduced pressure, precipitating a crystalline product. The crystalline product was dried under reduce pressure, to give 1.83 g (isolated yield: 98.1%, purity: 98% in terms of area percentage determined by high performance liquid chromatography) of methyl 5-methoxy-4-(3-bromopropoxy)anthranilate.

Methyl 5-methoxy-4-(3-bromopropoxy)anthranilate was a new compound and had the following characteristics.
m.p.: 100-101° C.
$^1$H-NMR (CDCl$_3$, δ (ppm)): 2.34-2.43 (2H, m), 3.56-3.63 (2H, m), 3.75 (3H, s), 3.96 (3H, s), 5.55 (2H, brs), 6.18 (1H, s), 7.31 (1H, s)

Reference Example III-7

Preparation of 4-(3-chloropropoxy)-3-methoxybenzoic acid

In a 300 mL volume glass flask equipped with a stirrer, a thermometer and a dropping funnel were placed 18.2 g (69.7 mmol) of methyl 4-(3-chloropropoxy)-3-methoxybenzoate (purity: 98 wt. %) prepared by procedures similar to the procedures of Reference Example III-3, 69.7 mL of an aqueous sodium hydroxide (2 mol/L), and 69.7 mL of methanol. The resulting mixture was heated to 40° C. for 4 hours in an argon gas atmosphere. After the reaction was complete, the reaction mixture was cooled to 10° C. and neutralized by 69.7 mL of hydrochloric acid (2 mol/L), to precipitate a crystalline product. The crystalline product was collected by filtration and dried under reduced pressure. There was obtained 16.2 g (isolated yield: 93.8%, purity: 99% in terms of area percentage determined by high performance liquid chromatography) of 4-(3-chloropropoxy)-3-methoxybenzoic acid as a white crystalline product.

4-(3-Chloropropoxy)-3-methoxybenzoic acid had the following characteristics.

m.p.: 150-152° C.

$^1$H-NMR (CDCl$_3$, δ (ppm)): 3.23-3.35 (2H, m), 3.68-3.88 (2H, m), 3.93 (3H, s), 4.35 (2H, t, J=3.0 Hz), 6.95 (1H, d, J=6.0 Hz), 7.57 (1H, s), 7.70 (1H, d, J=6.0 Hz)

Reference Example III-8

Preparation of
5-methoxy-4-(3-chloropropoxy)-2-nitrobenzoic acid

In a 50 mL volume glass flask equipped with a stirrer, a thermometer and a dropping funnel were placed 16.2 g (65.4 mmol) of 4-(3-chloropropoxy)-3-methoxybenzoic acid (purity: 98%) obtained in Reference Example III-7, 0.45 g (6.54 mmol) of sodium nitrite, and 20 mL of acetic acid. The resulting mixture was heated to 40° C. under stirring. To the reaction mixture was dropwise added slowly 27.6 g (262.0 mmol) of nitric acid (60 wt. %), and the mixture was heated at the same temperature for 5 hours. After the reaction was complete, 20 mL of water was added to the reaction mixture, and the aqueous mixture was cooled to 20° C., precipitating a crystalline product. The crystalline product was collected by filtration, washed with 30 mL of water, and dried under reduced pressure, to give 17.9 g (isolated yield: 93.0%, purity: 99% in terms of area percentage determined by high performance liquid chromatography) of 5-methoxy-4-(3-chloropropoxy)-2-nitrobenzoic acid as a white crystalline product.

5-Methoxy-4-(3-chloropropoxy)-2-nitrobenzoic acid had the following characteristics.

m.p.: 155-156° C.

$^1$H-NMR (CDCl$_3$, δ (ppm)): 2.37-2.45 (2H, m), 3.60-3.66 (2H, m), 3.90 (3H, s), 3.96 (3H, s), 7.08 (1H, s), 7.50 (1H, s)

Example III-9

Preparation of
5-methoxy-4-(3-chloropropoxy)anthranilic acid

In a 50 mL volume glass flask equipped with a stirrer, a thermometer, a reflux condenser and a gas inlet were placed 2.04 g (6.90 mmol) of 5-methoxy-4-(3-chloropropoxy)-2-nitrobenzoic acid (purity: 99%) obtained in Reference Example III-8 and 40 mL of methanol. The resulting mixture was heated to 40° C. under stirring. To the mixture was added 0.2 g of 5 wt. % palladium/carbon (containing 49% water) at the same temperature. The resulting mixture was heated to the same temperature for 2 hours, while hydrogen was introduced into the mixture under atmospheric pressure at a rate of 50 mL/min. After the reaction was complete, the reaction mixture was filtered and the filtrate was concentrated under reduced pressure, to precipitate a crystalline product. The crystalline product was dried under reduced pressure, to give 1.83 g (isolated yield: 97.0%, purity: 98% in terms of area percentage determined by high performance liquid chromatography) of 5-methoxy-4-(3-chloropropoxy)anthranilic acid as a white crystalline product.

5-Methoxy-4-(3-chloropropoxy)anthranilic acid had the following characteristics.

m.p.: 164-165° C.

$^1$H-NMR (CDCl$_3$, δ (ppm)): 2.15-2.23 (2H, m), 3.60 (3H, s), 3.80-4.00 (2H, m), 4.04 (2H, t, J=6.0 Hz), 6.36 (1H, s), 7.15 (1H, s), 8.05 (2H, brs), 8.10 (1H, brs)

Reference Example III-9

Preparation of methyl
4-(4-chlorobutoxy)-3-methoxybenzoate

In a 100 mL volume glass flask equipped with a stirrer, a thermometer and a reflux condenser were placed 10.2 g (54.9 mmol) of methyl 4-hydroxy-3-methoxybenzoate (purity: 98 wt. %), 12.5 g (71.4 mmol) of 4-bromo-1-chlorobutane, 8.3 g (60.4 mmol) of potassium carbonate (purity: 98 wt. %), and 300 mL of acetonitrile. The resulting mixture was refluxed under stirring at 80-85° C. for 8 hours in an argon gas atmosphere. After the reaction was complete, the reaction mixture was filtered and concentrated under reduced pressure. The concentrate was purified by silica gel column chromatography (gel: Wako gel C-200, eluent: n-hexane), to give 13.6 g (isolated yield: 90.0%, purity: 99% in terms of area percentage by high performance liquid chromatography) of methyl 4-(4-chlorobutoxy)-3-methoxybenzoate as a colorless liquid.

Methyl 4-(4-chlorobutoxy)-3-methoxybenzoate had the following characteristics.

$^1$H-NMR (CDCl$_3$, δ (ppm)): 1.96-2.07 (4H, m), 3.61-3.67 (2H, m), 3.89 (3H, s), 3.93 (3H, s), 4.13 (2H, t, J=6.0 Hz), 6.87 (1H, d, J=6.0 Hz), 7.55 (1H, s), 7.64 (1H, d, J=7 Hz)

Reference Example III-10

Preparation of methyl
5-methoxy-4-(4-chlorobutoxy)-2-nitrobenzoate

In a 50 mL volume glass flask equipped with a stirrer, a thermometer and a dropping funnel were placed 10.1 g (36.7 mmol) of methyl 4-(4-chlorobutoxy)-3-methoxybenzoate (purity: 98%) obtained in Reference Example III-9, 0.25 g (3.67 mmol) of sodium nitrite, and 12.5 mL of acetic acid. The resulting mixture was heated to 40° C. under stirring. To the reaction mixture was dropwise added slowly 115.4 g (146.8 mmol) of nitric acid (60 wt. %), and the mixture was heated at the same temperature for 5 hours. After the reaction was complete, 20 mL of water was added to the reaction mixture, and the aqueous mixture was cooled to 20° C., precipitating a crystalline product. The crystalline product was collected by filtration, washed successively with 30 mL of water and 30 mL of n-heptane, and dried under reduced pressure, to give 10.9 g (isolated yield: 92.0%, purity: 99% in terms of area percentage determined by high performance liquid chromatography) of methyl 5-methoxy-4-(4-chlorobutoxy)-2-nitrobenzoate as a white crystalline product.

Methyl 5-methoxy-4-(4-chlorobutoxy)-2-nitrobenzoate was a new compound and had the following characteristics.

m.p.: 74-75° C.

$^1$H-NMR (CDCl$_3$, δ (ppm)): 1.95-2.10 (4H, m), 3.61-3.66 (2H, m), 3.89 (3H, s), 3.93 (3H, s), 4.13 (2H, t, J=6.0 Hz), 6.87 (1H, d, J=6.0 Hz), 7.26 (1H, s), 7.44 (1H, s)

Example III-10

Preparation of methyl
5-methoxy-4-(4-chlorobutoxy)anthranilate

In a 50 mL volume glass flask equipped with a stirrer, a thermometer, a reflux condenser and a gas inlet were placed 2.02 g (6.29 mmol) of methyl 5-methoxy-4-(4-chlorobutoxy)-2-nitrobenzoate (purity: 99%) obtained in Reference Example III-10, and 40 mL of methanol. The resulting mixture was heated to 40° C. under stirring. To the mixture was added 0.2 g of 5 wt. % palladium/carbon (containing 49% water) at the same temperature. The resulting mixture was heated to the same temperature for 2 hours, while hydrogen was introduced into the mixture under atmospheric pressure at a rate of 50 mL/min. After the reaction was complete, the reaction mixture was filtered and the filtrate was concentrated under reduced pressure, to precipitate a crystalline product. The crystalline product was dried under reduced pressure, to give 1.81 g (isolated yield: 98.1%, purity: 98% in terms of area percentage determined by high performance liquid chromatography) of methyl 5-methoxy-4-(4-chlorobutoxy)anthranilate as a white crystalline product.

Methyl 5-methoxy-4-(4-chlorobutoxy)anthranilate was a new compound and had the following characteristics.

m.p.: 85-86° C.

$^1$H-NMR (CDCl$_3$, δ (ppm)): 1.92-2.90 (4H, m), 3.61-3.65 (2H, m), 3.76 (3H, s), 3.93 (3H, s), 4.03 (2H, t, J=6.0 Hz), 5.47 (2H, brs), 6.13 (1H, s), 7.31 (1H, s)

Reference Example III-11

Preparation of methyl
3-(3-chloropropoxy)-4-methoxybenzoate

In a 100 mL volume glass flask equipped with a stirrer, a thermometer and a reflux condenser were placed 10.2 g (54.9 mmol) of methyl 3-hydroxy-4-methoxybenzoate (purity: 98 wt. %), 11.2 g (71.4 mmol) of 3-bromo-1-chloropropane, 8.3 g (60.4 mmol) of potassium carbonate (purity: 98 wt. %), and 30 mL of acetone. The resulting mixture was refluxed under stirring at 80-85° C. for 8 hours in an argon gas atmosphere. After the reaction was complete, the reaction mixture was filtered. To the concentrate was added n-heptane, to precipitate a crystalline product. The crystalline product was collected and dried under reduced pressure, to give 13.7 g (isolated yield: 95.8%, purity: 99% in terms of area percentage by high performance liquid chromatography) of methyl 3-(3-chloropropoxy)-4-methoxybenzoate as a white crystalline product.

Methyl 3-(3-chloropropoxy)-4-methoxybenzoate had the following characteristics.

m.p.: 46-48° C.

$^1$H-NMR (CDCl$_3$, δ (ppm)): 2.27-2.33 (2H, m), 3.64-3.75 (2H, m), 3.79 (3H, s), 3.91 (3H, s), 4.21 (2H, t, J=5.0 Hz), 6.88 (1H, d, J=6.0 Hz), 7.67 (1H, d, J=6.0 Hz), 7.58 (1H, s), 7.70 (1H, d, J=6.0 Hz)

Reference Example III-12

Preparation of methyl
4-methoxy-5-(3-chloropropoxy)-2-nitrobenzoate

In a 50 mL volume glass flask equipped with a stirrer, a thermometer and a dropping funnel were placed 10.1 g (38.7 mmol) of methyl 3-(3-chloropropoxy)-4-methoxybenzoate (purity: 99%) obtained in Reference Example III-11, 0.27 g (3.87 mmol) of sodium nitrite, and 12.5 mL of acetic acid. The resulting mixture was heated to 40° C. under stirring. To the reaction mixture was dropwise added slowly 16.2 g (154.8 mmol) of nitric acid (60 wt. %), and the mixture was heated at the same temperature for 5 hours. After the reaction was complete, 20 mL of water was added to the reaction mixture, and the aqueous mixture was cooled to 20° C., precipitating a crystalline product. The crystalline product was collected by filtration, washed successively with 30 mL of water and 30 mL of n-heptane, and dried under reduced pressure, to give 11.3 g (isolated yield: 95.0%, purity: 99% in terms of area percentage determined by high performance liquid chromatography) of methyl 4-methoxy-5-(3-chloropropoxy)-2-nitrobenzoate as a white crystalline product.

Methyl 4-methoxy-5-(3-chloropropoxy)-2-nitrobenzoate had the following characteristics.

m.p.: 63-64° C.

$^1$H-NMR (CDCl$_3$, δ (ppm)): 2.28-2.37 (2H, m), 3.64-3.75 (2H, m), 3.89 (3H, s), 3.99 (3H, s), 4.24 (2H, t, J=5.0 Hz), 7.11 (1H, s), 7.45 (1H, s)

Example III-11

Preparation of methyl
4-methoxy-5-(3-chloropropoxy)anthranilate

In a 50 mL volume glass flask equipped with a stirrer, a thermometer, a reflux condenser and a gas inlet were placed 2.02 g (6.58 mmol) of methyl 4-methoxy-5-(3-chloropropoxy)-2-nitrobenzoate (purity: 99%) obtained in Reference Example III-12, and 40 mL of methanol. The resulting mixture was heated to 40° C. under stirring. To the mixture was added 0.2 g of 5 wt. % palladium/carbon (containing 49% water) at the same temperature. The resulting mixture was heated to the same temperature for 2 hours, while hydrogen was introduced into the mixture under atmospheric pressure at a rate of 50 mL/min. After the reaction was complete, the reaction mixture was filtered and the filtrate was concentrated under reduced pressure, to precipitate a crystalline product. The crystalline product was dried under reduced pressure, to give 1.80 g (isolated yield: 98.1%, purity: 98% in terms of area percentage determined by high performance liquid chromatography) of methyl 4-methoxy-5-(3-chloropropoxy)anthranilate as a white crystalline product.

Methyl 4-methoxy-5-(3-chloropropoxy)anthranilate had the following characteristics.

m.p.: 92-93° C.

$^1$H-NMR (CDCl$_3$, δ (ppm)): 2.19-2.27 (2H, m), 2.73-2.76 (2H, m), 3.80 (3H, s), 3.84 (3H, s), 4.09 (2H, t, J=6.0 Hz), 5.59 (2H, brs), 6.13 (1H, s), 7.37 (1H, s)

Reference Example III-13

Preparation of
3-(3-chloropropoxy)-4-methoxybenzoic acid

In a 300 mL volume glass flask equipped with a stirrer, a thermometer and a dropping funnel were placed 18.2 g (69.7 mmol) of methyl 3-(3-chloropropoxy)-4-methoxybenzoate, 69.7 mL of aqueous sodium hydroxide solution (2 mol/L), and 69.7 mL of methanol. The resulting mixture was heated to 40° C. for 4 hours in an argon gas atmosphere. After the reaction was complete, the reaction mixture was cooled to 10° C., and neutralized by 69.7 mL of hydrochloric acid (2 mol/L), to precipitate a crystalline product. The crystalline product was collected and dried under reduced pressure, to give 7.2 g (isolated yield: 95.8%, purity: 99% in terms of area percentage by high performance liquid chromatography) of 3-(3-chloropropoxy)-4-methoxybenzoic acid as a white crystalline product.

3-(3-Chloropropoxy)-4-methoxybenzoic acid had the following characteristics.

m.p.: 152-153° C.

$^1$H-NMR (CDCl$_3$, δ (ppm)): 2.14-2.23 (2H, m), 3.64-3.75 (2H, m), 3.79 (3H, s), 3.91 (3H, s), 4.12 (2H, t, J=5.0 Hz), 7.04 (1H, d, J=5.0 Hz), 7.45 (1H, s), 7.70 (1H, d, J=6.0 Hz), 12.5 (1H, brs)

Reference Example III-14

Preparation of 4-methoxy-5-(3-chloropropoxy)-2-nitrobenzoic acid

In a 50 mL volume glass flask equipped with a stirrer, a thermometer and a dropping funnel were placed 9.57 g (38.7 mmol) of 3-(3-chloropropoxy)-4-methoxybenzoic acid (purity: 99%) obtained in Reference Example III-13, 0.27 g (3.87 mmol) of sodium nitrite, and 12.5 mL of acetic acid. The resulting mixture was heated to 40° C. under stirring. To the reaction mixture was dropwise added slowly 16.2 g (154.8 mmol) of nitric acid (60 wt. %), and the mixture was heated at the same temperature for 5 hours. After the reaction was complete, 20 mL of water was added to the reaction mixture, and the aqueous mixture was cooled to 20° C., precipitating a crystalline product. The crystalline product was collected by filtration, washed successively with 30 mL of water and 30 mL of n-heptane, and dried under reduced pressure, to give 10.4 g (isolated yield: 92.0%, purity: 99% in terms of area percentage determined by high performance liquid chromatography) of 4-methoxy-5-(3-chloropropoxy)-2-nitrobenzoic acid as a white crystalline product. 4-Methoxy-5-(3-chloropropoxy)-2-nitrobenzoic acid had the following characteristics.

m.p.: 162-163° C.

$^1$H-NMR (CDCl$_3$, δ (ppm)): 1.98-2.25 (2H, m), 3.65-3.75 (2H, m), 3.89 (3H, s), 3.94 (3H, s), 4.24 (2H, t, J=5.0 Hz), 7.33 (1H, s), 8.31 (1H, s), 13.5 (1H, brs)

Example III-12

Preparation of 4-methoxy-5-(3-chloropropoxy)anthranilic acid

In a 50 mL volume glass flask equipped with a stirrer, a thermometer, a reflux condenser and a gas inlet were placed 4.00 g (13.5 mmol) of 4-methoxy-5-(3-chloropropoxy)-2-nitrobenzoic acid (purity: 99%) obtained in Reference Example III-14, and 40 mL of methanol. The resulting mixture was heated to 40° C. under stirring. To the mixture was added 0.4 g of 5 wt. % palladium/carbon (containing 49% water) at the same temperature. The resulting mixture was heated to the same temperature for 4 hours, while hydrogen was introduced into the mixture under atmospheric pressure at a rate of 50 mL/min. After the reaction was complete, the reaction mixture was filtered and the filtrate was concentrated under reduced pressure, to precipitate a crystalline product. The crystalline product was dried under reduced pressure, to give 3.52 g (isolated yield: 98.1%, purity: 98% in terms of area percentage determined by high performance liquid chromatography) of 4-methoxy-5-(3-chloropropoxy)-anthranilic acid as a white crystalline product.

4-Methoxy-5-(3-chloropropoxy)anthranilic acid was a new compound and had the following characteristics.

m.p.: 115-116° C.

$^1$H-NMR (CDCl$_3$, δ (ppm)): 2.05-2.13 (2H, m), 3.50 (3H, s), 3.74-3.90 (4H, m), 4.35 (2H, t, J=6.0 Hz), 6.30 (1H, s), 7.43 (1H, s), 8.30 (2H, brs), 8.32 (1H, brs)

Reference Example III-15

Preparation of 4-(2-chloroethoxy)-3-methoxybenzoic acid

In a 300 mL volume glass flask equipped with a stirrer, a thermometer and a dropping funnel were placed 17.40 g (69.7 mmol) of methyl 4-(2-chloroethoxy)-3-methoxybenzoate, 69.7 mL of aqueous sodium hydroxide solution (2 mol/L), and 69.7 mL of methanol. The resulting mixture was heated to 40° C. for 4 hours in an argon gas atmosphere. After the reaction was complete, the reaction mixture was cooled to 10° C., and neutralized by 69.7 mL of hydrochloric acid (2 mol/L). The reaction mixture was then placed to distill methanol off, and cooled to 10° C., to precipitate a crystalline product. The crystalline product was collected and dried under reduced pressure, to give 15.5 g (isolated yield: 95.2%, purity: 99% in terms of area percentage by high performance liquid chromatography) of 4-(2-chloroethoxy)-3-methoxybenzoic acid as a white crystalline product.

4-(2-Chloroethoxy)-3-methoxybenzoic acid had the following characteristics.

m.p.: 205-206° C.

$^1$H-NMR (CDCl$_3$, δ (ppm)): 3.84 (3H, s), 3.93-4.01 (2H, m), 4.31-4.33 (2H, m), 7.06 (1H, s), 7.47 (1H, s), 7.55 (1H, s), 12.73 (1H, brs)

Reference Example III-16

Preparation of 5-methoxy-4-(2-chloroethoxy)-2-nitrobenzoic acid

In a 50 mL volume glass flask equipped with a stirrer, a thermometer and a dropping funnel were placed 9.0 g (38.7 mmol) of 4-(2-chloroethoxy)-3-methoxybenzoic acid (purity: 99%) obtained in Reference Example III-15, 0.27 g (3.87 mmol) of sodium nitrite, and 12.5 mL of acetic acid. The resulting mixture was heated to 40° C. under stirring. To the reaction mixture was dropwise added slowly 16.2 g (154.8 mmol) of nitric acid (60 wt. %), and the mixture was heated at the same temperature for 10 hours. After the reaction was complete, 20 mL of water was added to the reaction mixture, and the aqueous mixture was cooled to 20° C., precipitating a crystalline product. The crystalline product was collected by filtration, washed successively with 30 mL of water and 30 mL of n-heptane, and dried under reduced pressure, to give 9.91 g (isolated yield: 92.0, purity: 99% in terms of area percentage determined by high performance liquid chromatography) of 5-methoxy-4-(2-chloroethoxy)-2-nitrobenzoic acid as a white crystalline product.

5-Methoxy-4-(2-chloroethoxy)-2-nitrobenzoic acid had the following characteristics.

m.p.: 172-173° C.

$^1$H-NMR (CDCl$_3$, δ (ppm)): 3.91 (3H, s), 3.93-4.01 (2H, m), 4.41-4.47 (2H, m), 7.33 (1H, s), 7.61 (1H, s), 13.6 (1H, brs)

Example III-13

Preparation of 5-methoxy-4-(2-chloroethoxy)anthranilic acid

In a 50 mL volume glass flask equipped with a stirrer, a thermometer, a reflux condenser and a gas inlet were placed 3.76 g (13.5 mmol) of 5-methoxy-4-(2-chloroethoxy)-2-nitrobenzoic acid (purity: 99%) obtained in Reference Example III-16, 40 mL of methanol, and 0.4 g of 5 wt. % palladium/carbon (containing 49% water). The resulting mixture was heated to 40° C. under stirring, and further heated to the same temperature for 4 hours, while hydrogen was introduced into the mixture under atmospheric pressure at a rate of 50 mL/min. After the reaction was complete, the reaction mixture was filtered and the filtrate was concentrated under reduced pressure, to precipitate a crystalline product. The crystalline product was dried under reduced pressure, to give 3.27 g (isolated yield: 98.1%, purity: 99% in terms of area percentage determined by high performance liquid chromatography) of 5-methoxy-4-(2-chloroethoxy)anthranilic acid as a white crystalline product.

5-Methoxy-4-(2-chloroethoxy)anthranilic acid had the following characteristics.

m.p.: 182-183° C.

$^1$H-NMR (CDCl$_3$, δ (ppm)): 3.70 (3H, s), 3.93-3.97 (2H, m), 4.18-4.21 (2H, m), 6.31 (1H, s), 7.15 (1H, s), 8.31 (2H, brs), 8.35 (1H, brs)

Example IV-1

Preparation of
6-methoxy-7-(3-chloropropoxy)quinazolin-4-one

In a 1,000 mL volume stainless pressure-resistant vessel equipped with a stirrer, a thermometer and a pressure gauge were placed 161.5 g (0.59 mol) of methyl 5-methoxy-4-(3-chloropropoxy)anthranilate, 156.5 g (1.48 mol) of methyl orthoformate, 113.7 g (1.48 mol) of ammonium acetate, and 300 mL of methanol. The vessel was closed, and the reaction was carried out at 90-95° C. for 8 hours. The pressure in the vessel was 0.1-0.3 MPa (gauge pressure). After the reaction was complete, 600 mL of water was added to the reaction mixture. The aqueous reaction mixture was stirred at 0-10° C. for one hour, to precipitate a crystalline product. The crystalline product was collected by filtration, washed with 600 mL of water, and dried at 60° C. under reduced pressure, to give 152.8 g (isolated yield: 94%) of 6-methoxy-7-(3-chloropropoxy)quinazolin-4-one as a white crystalline product.

6-Methoxy-7-(3-chloropropoxy)quinazolin-4-one was a new compound and had the following characteristics.

m.p.: 259° C.

CI-MS (m/e): 269 (M+1)

$^1$H-NMR (DMSO-d$_6$, δ (ppm)): 2.19-2.28 (2H, m), 3.80 (2H, t, J=6.6 Hz), 3.88 (3H, s), 4.22 (2H, t, J=6.0 Hz), 7.16 (1H, s), 7.46 (1H, s), 11.0 (1H, brs)

$^{13}$C-NMR (DMSO-d$_6$, δ (ppm)): 31.4, 41.8, 55.7, 65.2, 105.1, 108.7, 115.7, 143.8, 144.7, 148.5, 153.4, 160.0

Elemental Analysis:
Found: C, 53.41%; H, 4.90%; N, 10.05%.
Theoretical for C$_{12}$H$_{13}$ClN$_2$O$_3$: C, 53.64%; H, 4.88%; N, 10.43%.

Example IV-2

Preparation of
7-methoxy-6-(3-chloropropoxy)quinazolin-4-one

In a 10 mL volume stainless pressure-resistant vessel equipped with a stirrer and a thermometer were placed 1.0 g (3.7 mmol) of methyl 4-methoxy-5-(3-chloropropoxy)-anthranilate, 0.93 g (8.8 mmol) of methyl orthoformate, 0.67 g (8.8 mmol) of ammonium acetate, and 5 mL of methanol. The vessel was closed, and the reaction was carried out at 90-95° C. for 8 hours. After the reaction was complete, 50 mL of water was added to the reaction mixture. The aqueous reaction mixture was stirred at 25° C. for one hour, to precipitate a crystalline product. The crystalline product was collected by filtration and dried at 60° C. under reduced pressure, to give 0.89 g (isolated yield: 91%) of 7-methoxy-6-(3-chloropropoxy)quinazolin-4-one as a white crystalline product.

7-Methoxy-6-(3-chloropropoxy)quinazolin-4-one was a new compound and had the following characteristics.

CI-MS (m/e): 269 (M+1)

$^1$H-NMR (DMSO-d$_6$, δ (ppm)): 2.19-2.82 (2H, m), 3.80 (2H, t, J=6.6 Hz), 3.91 (3H, s), 4.19 (2H, t, J=6.0 Hz), 7.15 (1H, s), 7.47 (1H, s), 7.99 (1H, s), 11.0 (1H, brs) nitrobenzoate as a white crystalline product.

Example IV-3

Preparation of
6-methoxy-7-(2-chloroethoxy)quinazolin-4-one

In a 10 mL volume stainless pressure-resistant vessel equipped with a stirrer and a thermometer were placed 1.0 g (3.9 mmol) of methyl 5-methoxy-4-(3-chloroethoxy)-anthranilate, 1.02 g (9.6 mmol) of methyl orthoformate, 0.74 g (9.6 mmol) of ammonium acetate, and 5 mL of methanol. The vessel was closed, and the reaction was carried out at 90-95° C. for 8 hours. After the reaction was complete, 50 mL of water was added to the reaction mixture. The aqueous reaction mixture was stirred at 25° C. for one hour, to precipitate a crystalline product. The crystalline product was collected by filtration and dried at 60° C. under reduced pressure, to give 0.87 g (isolated yield: 89%) of 6-methoxy-7-(2-chloroethoxy)quinazolin-4-one as a gray crystalline product.

6-Methoxy-7-(2-chloroethoxy)quinazolin-4-one was a new compound and had the following characteristics.

CI-MS (m/e): 255 (M+1)

$^1$H-NMR (DMSO-d$_6$, δ (ppm)): 3.89 (3H, s), 4.01 (2H, t, J=5.5 Hz), 4.41 (2H, t, J=5.5 Hz), 7.16 (1H, s), 7.47 (1H, s), 7.99 (1H, s), 11.0 (1H, brs)

Example IV-4

Preparation of
6-methoxy-7-(4-chlorobutoxy)quinazolin-4-one

In a 10 mL volume stainless pressure-resistant vessel equipped with a stirrer and a thermometer were placed 1.1 g (3.5 mmol) of methyl 5-methoxy-4-(4-chlorobutoxy)-anthranilate, 0.92 g (8.8 mmol) of methyl orthoformate, 0.67 g (8.8 mmol) of ammonium acetate, and 5 mL of methanol. The vessel was closed, and the reaction was carried out at 90-95° C. for 8 hours. After the reaction was complete, 50 mL of water was added to the reaction mixture. The aqueous reaction mixture was stirred at 25° C. for one hour, to precipitate a crystalline product. The crystalline product was collected by filtration and dried at 60° C. under reduced pressure, to give 0.94 g (isolated yield: 96%) of 6-methoxy-7-(4-chlorobutoxy)quinazolin-4-one as a gray crystalline product.

6-Methoxy-7-(4-chlorobutoxy)quinazolin-4-one was a new compound and had the following characteristics.

CI-MS (m/e): 283 (M+1)

$^1$H-NMR (DMSO-d$_6$, δ (ppm)): 1.88-1.92 (4H, m), 3.72-3.76 (2H, m), 3.87 (3H, s), 4.13-4.15 (2H, m), 7.14 (1H, s), 7.44 (1H, s), 7.98 (1H, s), 12.1 (1H, brs)

Reference Example V-1

Preparation of
6-methoxy-7-(3-chloropropoxy)quinazolin-4-one

In a 1,000 mL volume stainless pressure-resistant vessel equipped with a stirrer, a thermometer and a pressure gauge were placed 161.5 g (0.59 mol) of methyl 5-methoxy-4-(3-chloropropoxy)anthranilate, 156.5 g (1.48 mol) of methyl orthoformate, 113.7 g (1.48 mol) of ammonium acetate, and 300 mL of methanol. The vessel was closed, and the reaction was carried out at 90-95° C. for 8 hours. The pressure in the vessel was 0.1-0.3 MPa (gauge pressure). After the reaction was complete, 600 mL of water was added to the reaction mixture. The aqueous reaction mixture was stirred at 0-10° C. for one hour, to precipitate a crystalline product. The crystalline product was collected by filtration, washed with 600 mL of water, and dried at 60° C. under reduced pressure, to give 152.8 g (isolated yield: 94%) of 6-methoxy-7-(3-chloropropoxy)quinazolin-4-one as a white crystalline product.

6-Methoxy-7-(3-chloropropoxy)quinazolin-4-one was a new compound and had the following characteristics.

m.p.: 259° C.

CI-MS (m/e): 269 (M+1)

$^1$H-NMR (DMSO-d$_6$, δ (ppm)): 2.19-2.28 (2H, m), 3.80 (2H, t, J=6.6 Hz), 3.88 (3H, s), 4.22 (2H, t, J=6.0 Hz), 7.16 (1H, s), 7.46 (1H, s), 11.0 (1H, brs)

$^{13}$C-NMR (DMSO-d$_6$, δ (ppm)): 31.4, 41.8, 55.7, 65.2, 105.1, 108.7, 115.7, 143.8, 144.7, 148.5, 153.4, 160.0

Elemental Analysis:

Found: C, 53.41%; H, 4.90%; N, 10.05%.

Theoretical for $C_{12}H_{13}ClN_2O_3$: C, 53.64%; H, 4.88%; N, 10.43%

Example V-1

Preparation of
6-methoxy-7-(3-morpholinopropoxy)quinazolin-4-one

In a 500 mL volume glass vessel equipped with a stirrer, a thermometer and a reflux condenser were placed 95.0 g (0.354 mol) of 6-methoxy-7-(3-chloropropoxy)-quinazolin-4-one, 154.2 g (1.77 mol) of morpholine, and 380 mL of sec-butyl alcohol. The resulting mixture was heated to 105° C. under stirring for 18 hours. After the reaction was complete, 380 mL of methanol was added to the reaction mixture. The resulting mixture was stirred at 70° C. for 30 minutes, and cooled to room temperature. The mixture was then stirred for 30 minutes at room temperature. The precipitated crystalline product was filtered, placed in 190 mL of methanol and stirred for washing, again filtered, and dried at 60° C. under reduced pressure to give 104 g (isolated yield: 92%, purity: 98.81% in terms of area percentage determined by high performance liquid chromatography) of 6-methoxy-7-(3-morpholinopropoxy)quinazolin-4-one as a white crystalline product.

6-Methoxy-7-(3-morpholinopropoxy)quinazolin-4-one had the following characteristics.

CI-MS (m/e): 320 (M+1)

$^1$H-NMR (DMSO-d$_6$, δ (ppm)): 2.08-2.13 (2H, m), 2.48 (4H, t, J=4.5 Hz), 2.56 (2H, t, J=6.9 Hz), 3.73 (4H, t, J=4.5 Hz), 4.00 (3H, s), 4.24 (2H, t, J=6.6 Hz), 7.18 (1H, s), 7.60 (1H, s), 8.02 (1H, s), 10.5 (1H, brs)

Elemental Analysis:

Found: C, 59.71%; H, 6.62%; N, 13.10%.

Theoretical for $C_{16}H_{21}N_3O_4$: C, 60.17%; H, 6.63%; N, 13.10%

Example V-2

Preparation of
6-methoxy-7-(3-morpholinopropoxy)quinazolin-4-one hydrochloride

In a 1,000 mL volume glass vessel equipped with a stirrer, a thermometer and a reflux condenser were placed 90 g (0.284 mol) of 6-methoxy-7-(3-chloropropoxy)quinazolin-4-one prepared by procedures similar to those of Reference Example V-1, 94 mL (1.13 mol) of hydrochloric acid (12 mol/L, and 180 mL of methanol. The resulting mixture was stirred for one hour at room temperature. After the reaction was complete, 360 mL of acetone was added to the reaction mixture. The resulting mixture was cooled to 5° C. and stirred for one hour. The precipitated crystalline product was filtered to give 113 g of 6-methoxy-7-(3-morpholinopropoxy)quinazolin-4-one hydrochloride as a crude crystalline product (purity: 99.16% in terms of area percentage determined by high performance liquid chromatography). Subsequently, 105 g of the crude crystalline product was mixed with 700 mL of methanol. The mixture was stirred at 60° C. for one hour. After the stirring was complete, the mixture was cooled to room temperature, to precipitate a crystalline product. The crystalline product was collected by filtration and dried under reduced pressure to give 98 g of 6-methoxy-7-(3-morpholinopropoxy)quinazolin-4-one hydrochloride (purity: 99.74% in terms of area percentage determined by high performance liquid chromatography).

Example V-3

Preparation of
6-methoxy-7-(3-morpholinopropoxy)quinazolin-4-one

In a 25 mL volume glass vessel equipped with a stirrer, a thermometer and a reflux condenser were placed 2.0 g (7.4 mmol) of 6-methoxy-7-(3-chloropropoxy)quinazolin-4-one prepared by procedures similar to those of Reference Example V-1, and 6.45 g (74 mmol) of morpholine. The resulting mixture was stirred at 105° C. for 4 hours. After the reaction was complete, the reaction mixture was analyzed by high performance liquid chromatography (absolute quantitative analysis). There was produced 2.17 g (reaction yield: 92%) of 6-methoxy-7-(3-morpholinopropoxy)quinazolin-4-one.

Example V-4

Preparation of
6-methoxy-7-(3-morpholinopropoxy)quinazolin-4-one

In a 10 mL volume glass vessel equipped with a stirrer and a thermometer were placed 1.0 g (3.7 mmol) of 6-methoxy-7-(3-chloropropoxy)quinazolin-4-one prepared by procedures similar to those of Reference Example V-1, 1.61 g (18.5 mmol) of morpholine, and 4 mL of methanol. The resulting mixture was stirred at 105° C. for 4 hours. After the reaction was complete, the reaction mixture was analyzed by high performance liquid chromatography (absolute quantitative analysis). There was produced 1.10 g (reaction yield: 93%) of 6-methoxy-7-(3-morpholinopropoxy)quinazolin-4-one.

Example V-5

Preparation of
6-methoxy-7-(3-morpholinopropoxy)quinazolin-4-one

In a 5 mL volume glass vessel equipped with a stirrer and a thermometer were placed 0.5 g (1.9 mmol) of 6-methoxy-7-(3-chloropropoxy)quinazolin-4-one prepared by procedures similar to those of Reference Example V-1, 0.5 g (5.7 mmol) of morpholine, and 1.0 mL (4.0 mmol) of aqueous sodium hydroxide solution (4.0 mol/L). The resulting mixture was stirred at 50° C. for 2 hours. After the reaction was complete, the reaction mixture was analyzed by high performance liquid chromatography (absolute quantitative analysis). There was produced 0.57 g (reaction yield: 94%) of 6-methoxy-7-(3-morpholinopropoxy)-quinazolin-4-one.

Example V-6

Preparation of
6-methoxy-7-(3-piperidino-propoxy)quinazolin-4-one

In a 100 mL volume glass vessel equipped with a stirrer and a thermometer were placed 15.0 g (55.8 mmol) of 6-methoxy-7-(3-chloropropoxy)quinazolin-4-one prepared by procedures similar to those of Reference Example V-1, 13.85 g (163 mmol) of piperidine, and 27.4 mL (113.6 mmol) of aqueous sodium hydroxide solution (4.0 mol/L). The resulting mixture was stirred at 55° C. for 5 hours. After the reaction was complete, the reaction mixture was cooled to room temperature and placed under reduced pressure to distill unreacted piperidine off. To the residue was added 18.9 mL (113.4 mmol) of hydrochloric acid (6.0 mol/L), and the mixture was cooled to 0° C. The precipitated crystalline product was collected by filtration and dried at 60° C. under reduced pressure, to give 13.5 g (isolated yield: 76.3%) of 6-methoxy-7-(3-piperidino-propoxy)quinazolin-4-one.

6-Methoxy-7-(3-piperidinopropoxy)quinazolin-4-one had the following characteristics.

CI-MS (m/e): 318 (M+1)

$^1$H-NMR (DMSO-$d_6$, δ (ppm)): 1.45-1.47 (2H, m), 1.62 (4H, t, J=6.0 Hz), 2.10-2.14 (2H, m), 2.42-2.48 (4H, m), 2.57 (2H, t, J=6.6 Hz), 3.99 (3H, s), 4.21 (2H, t, J=6.3 Hz), 7.10 (1H, s), 7.56 (1H, s), 7.98 (1H, s), 10.5 (1H, brs)

Example V-7

Preparation of
6-methoxy-7-(3-piperidino-propoxy)quinazolin-4-one

In a 5 mL volume glass vessel equipped with a stirrer and a thermometer were placed 0.5 g (1.9 mmol) of 6-methoxy-7-(3-chloropropoxy)quinazolin-4-one prepared by procedures similar to those of Reference Example V-1, 0.81 g (9.5 mmol) of piperidine, and 4.8 mL (19 mmol) of aqueous sodium hydroxide solution (4.0 mol/L). The resulting mixture was stirred at 50° C. for 5 hours. After the reaction was complete, the reaction mixture was analyzed by high performance liquid chromatography (absolute quantitative analysis). There was produced 0.51 g (reaction yield: 85%) of 6-methoxy-7-(3-piperidinopropoxy)-quinazolin-4-one.

Example V-8

Preparation of
6-methoxy-7-(3-piperidino-propoxy)quinazolin-4-one

In a 5 mL volume glass vessel equipped with a stirrer and a thermometer were placed 1.0 g (3.7 mmol) of 6-methoxy-7-(3-chloropropoxy)quinazolin-4-one prepared by procedures similar to those of Reference Example V-1, 0.48 g (5.6 mmol) of piperidine, and 4.8 mL (19 mmol) of aqueous sodium hydroxide solution (4.0 mol/L). The resulting mixture was stirred at 50° C. for 5 hours. After the reaction was complete, the reaction mixture was analyzed by high performance liquid chromatography (absolute quantitative analysis). There was produced 1.05 g (reaction yield: 89%) of 6-methoxy-7-(3-piperidino-propoxy)-quinazolin-4-one.

Example V-9

Preparation of
6-methoxy-7-(3-piperidino-propoxy)quinazolin-4-one

In a 5 mL volume glass vessel equipped with a stirrer and a thermometer were placed 1.0 g (3.7 mmol) of 6-methoxy-7-(3-chloropropoxy)quinazolin-4-one prepared by procedures similar to those of Reference Example V-1, 1.62 g (19 mmol) of piperidine, and 10 mL of ethanol. The resulting mixture was stirred at 80° C. for 5 hours. After the reaction was complete, the reaction mixture was analyzed by high performance liquid chromatography (absolute quantitative analysis). There was produced 1.02 g (reaction yield: 87%) of 6-methoxy-7-(3-piperidinopropoxy)quinazolin-4-one.

Example V-10

Preparation of
6-methoxy-7-(3-piperidino-propoxy)quinazolin-4-one

In a 5 mL volume glass vessel equipped with a stirrer and a thermometer were placed 1.0 g (3.7 mmol) of 6-methoxy-7-(3-chloropropoxy)quinazolin-4-one prepared by procedures similar to those of Reference Example V-1, 1.62 g (19 mmol) of piperidine, and 10 mL of sec-butyl alcohol. The resulting mixture was stirred at 105° C. for 5 hours. After the reaction was complete, the reaction mixture was analyzed by high performance liquid chromatography (absolute quantitative analysis). There was produced 1.06 g (reaction yield: 90%) of 6-methoxy-7-(3-piperidinopropoxy)quinazolin-4-one.

Example V-11

Preparation of 6-methoxy-7-(3-thiomorpholinopropoxy)quinazolin-4-one

In a 100 mL volume glass vessel equipped with a stirrer and a thermometer were placed 4.0 g (14.9 mmol) of 6-methoxy-7-(3-chloropropoxy)quinazolin-4-one prepared by procedures similar to those of Reference Example V-1, 5.0 g (48.5 mmol) of thiomorpholine, and 16 mL of sec-butyl alcohol. The resulting mixture was stirred at 105° C. for 7.5 hours. After the reaction was complete, 16 mL of methanol was added to the reaction mixture. The reaction mixture was refluxed for one hour and cooled to room temperature. Thus precipitated crystalline product was collected by filtration and dried at 60° C. under reduced pressure, to give 4.38 g (isolated yield: 81%) of 6-methoxy-7-(3-thiomorpholinopropoxy)quinazolin-4-one.

6-Methoxy-7-(3-thiomorpholinopropoxy)quinazolin-4-one was a new compound and had the following characteristics.

CI-MS (m/e): 336 (M+1)

$^1$H-NMR (DMSO-$d_6$, δ (ppm)): 1.87-1.96 (2H, m), 2.44-2.52 (2H, m), 2.59-2.66 (8H, m), 3.87 (3H, s), 4.14 (2H, t, J=6.3 Hz), 7.12 (1H, s), 7.44 (1H, s), 7.98 (1H, s), 12.0 (1H, brs)

Example V-12

Preparation of 6-methoxy-7-[3-(2-methylpiperidinopropoxy)quinazolin-4-one

In a 100 mL volume glass vessel equipped with a stirrer, a thermometer and a reflux condenser were placed 19.6 g (73 mmol) of 6-methoxy-7-(3-chloropropoxy)quinazolin-4-one prepared by procedures similar to those of Reference Example V-1, 36.17 g (365 mmol) of 2-methylpiperidine, 9.8 mL (101.6 mmol) of 1-methyl-2-pyrrolidinone, and 79 mL of sec-butyl alcohol. The resulting mixture was stirred at 50-100° C. for 14 hours. After the reaction was complete, 80 mL of methanol was added to the reaction mixture. The reaction mixture was then stirred at 60-70° C. for 30 minutes and further stirred at 0-10° C. for 30 minutes. Thus precipitated crystalline product was collected by filtration, washed with 60 mL of acetone, dissolved in 118 mL of aqueous sodium hydroxide solution (1 mol/L), and stirred at 47° C. for 3 hours. The mixture was again filtered. To the filtrate were successively added 36 mL of water, 60 mL of 1-methyl-2-pyrrolidine, and 18.7 mL of hydrochloric acid (60 mol/L). The resulting mixture was stirred at 0-10° C. for 30 minutes. Thus precipitated crystalline product was collected by filtration and placed in a mixture of 118 mL of acetone and 118 mL of water. The aqueous mixture was stirred at 50-60° C. for one hour, further at 20-30° C. for 30 minutes, and filtered. The product collected by filtration was dried under reduced pressure, to give 17.0 g (isolated yield: 69%, purity: 98.70% in terms of area percentage determined by high performance liquid chromatography) of 6-methoxy-7-[3-(2-methylpiperidinopropoxy)quinazolin-4-one.

6-Methoxy-7-[3-(2-methylpiperidinopropoxy)quinazolin-4-one had the following characteristics.

CI-MS (m/e): 332 (M+1)

$^1$H-NMR (DMSO-$d_6$, δ (ppm)): 0.97 (3H, d, J=6.6 Hz), 1.02-1.30 (2H, m), 1.36-1.59 (4H, m), 1.72-1.91 (2H, m), 2.04-2.13 (1H, m), 2.24-2.39 (2H, m), 2.75-2.84 (2H, m), 3.86 (3H, s), 4.13 (2H, t, J=6.3 Hz), 7.11 (1H, s), 7.44 (1H, s), 7.97 (1H, s), 12.0 (1H, brs)

Example V-13

Preparation of 6-methoxy-7-[3-(4-methylpiperidinopropoxy)quinazolin-4-one

The procedures of Example V-12 were repeated except for replacing 2-methylpiperidine with 4-methylpiperidine. There was obtained 21.3 g (isolated yield: 87%, purity: 99.5% in terms of area percentage determined by high performance liquid chromatography) of 6-methoxy-7-[3-(4-methylpiperidinopropoxy)quinazolin-4-one.

6-Methoxy-7-[3-(4-methylpiperidinopropoxy)quinazolin-4-one had the following characteristics.

CI-MS (m/e): 332 (M+1)

$^1$H-NMR (DMSO-$d_6$, δ (ppm)): 0.88 (3H, d, J=6.0 Hz) 1.04-1.19 (2H, m), 1.27-1.34 (1H, m), 1.54-1.58 (2H, m), 1.81-1.95 (4H, m), 2.37-2.42 (2H, m), 2.80-2.84 (2H, m), 3.87 (3H, s), 4.11-4.15 (2H, m), 7.10 (1H, s), 7.44 (1H, s), 7.97 (1H, s), 12.0 (1H, brs)

UTILIZATION IN INDUSTRY

According to the invention, quinazolin-4-one compounds which are of value as intermediate compounds for preparing pharmaceuticals and agricultural chemicals can be prepared from anthranilic acid compounds in high yields under moderate conditions and by simple procedures. Accordingly, the disclosed processes are favorably employable in industry. Further, various compounds employable in industry as intermediate compounds for preparing pharmaceuticals and agricultural chemicals can be prepared by the present invention.

What is claimed is:

1. A process for preparing a quinazolin-4-one compound having the formula (2):

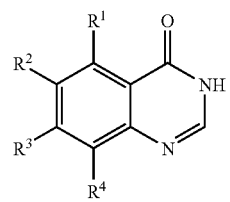

(2)

in which each of $R^1$, $R^2$, $R^3$ and $R^4$ independently represents a hydrogen atom, an alkyl group, a cycloalkyl group, an aralkyl group, an aryl group, a halogen atom, a hydroxyl group, an alkoxy group, an alkylthio group, nitro, cyano, or carbonyl, which comprises reacting an anthranilic acid compound having the formula (1):

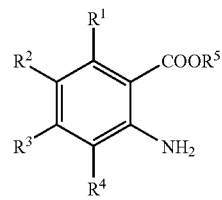

(1)

in which $R^1$, $R^2$, $R^3$ and $R^4$ have the same meaning as above, and $R^5$ represents a hydrogen atom or a hydrocarbyl group selected from the group consisting of methyl, ethyl, propyl, butyl, pentyl and hexyl, with methyl orthoformate or ethyl orthoformate in the presence of an ammonium carboxylate.

2. A process of claim 1 for preparing a 6-alkoxy-7-halogenoalkoxyquinazolin-4-one compound having the formula (4):

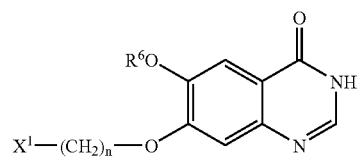

(4)

wherein $R^6$ represents an alkyl group, $X^1$ represents a halogen atom, and n is an integer of 2 to 4, which comprises reacting a 5-alkoxy-4-halogenoalkoxyanthranilic acid compound having the formula (3):

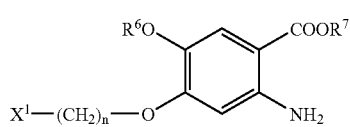

(3)

wherein each of $R^6$, $X^1$, and n has the same meaning as above, and $R^7$ represents a hydrogen atom or a hydrocarbyl group, with methyl orthoformate or ethyl orthoformate in the presence of an ammonium carboxylate.

3. A process of claim 1 for preparing a 7-alkoxy-6-halogenoalkoxyquinazolin-4-one compound having the formula (6):

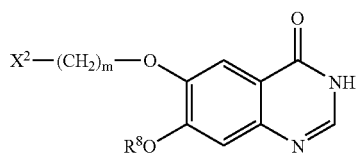

(6)

wherein $R^8$ represents an alkyl group, $X^2$ represents a halogen atom, and m is an integer of 2 to 4, which comprises reacting a 4-alkoxy-5-halogenoalkoxyanthranilic acid compound having the formula (5):

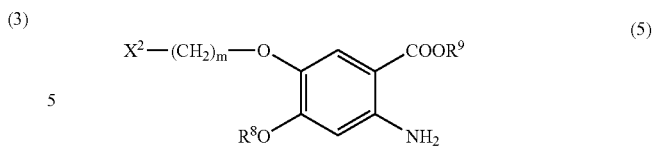

(5)

wherein each of $R^8$, $X^2$, and m has the same meaning as above, and $R^9$ represents a hydrogen atom or a hydrocarbyl group, with a formic acid derivative selected from the group consisting of formic acid, a formic acid ester and an orthoformic acid ester in the presence of an ammonium carboxylate.

4. The process of claim 3, wherein the formic acid derivative is an orthoformic acid ester.

5. The process of claim 1, wherein each of $R^1$, $R^2$ and $R^3$ is a hydrogen atom, and $R^2$ is an iodine atom.

6. The process of claim 1, wherein each of $R^1$ and $R^4$ is a hydrogen atom, and each of $R^2$ and $R^3$ is 2-methoxyethoxy.

7. The process of claim 1, wherein the ammonium carboxylate is ammonium acetate.

* * * * *